United States Patent
Boodagh et al.

(10) Patent No.: US 11,944,725 B2
(45) Date of Patent: Apr. 2, 2024

(54) PRO-HEALING, PRO-REGENERATIVE NANOFIBROUS COATING FOR MEDICAL IMPLANTS

(71) Applicant: THE REGENTS OF THE UNIVERSITY OF COLORADO, A BODY CORPORATE, Denver, CO (US)

(72) Inventors: Parnaz Boodagh, Boulder, CO (US); Wei Tan, Broomfield, CO (US); Michael Floren, Broomfield, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 593 days.

(21) Appl. No.: 17/255,879

(22) PCT Filed: Jun. 28, 2019

(86) PCT No.: PCT/US2019/039961
§ 371 (c)(1),
(2) Date: Dec. 23, 2020

(87) PCT Pub. No.: WO2020/006499
PCT Pub. Date: Jan. 2, 2020

(65) Prior Publication Data
US 2021/0260256 A1    Aug. 26, 2021

Related U.S. Application Data

(60) Provisional application No. 62/692,209, filed on Jun. 29, 2018.

(51) Int. Cl.
*A61L 27/50* (2006.01)
*A61L 31/10* (2006.01)
*A61L 31/16* (2006.01)

(52) U.S. Cl.
CPC .............. *A61L 31/10* (2013.01); *A61L 31/16* (2013.01); *A61L 27/507* (2013.01);
(Continued)

(58) Field of Classification Search
None
See application file for complete search history.

(56) References Cited

U.S. PATENT DOCUMENTS

2007/0162110 A1* 7/2007 Dave ................... A61L 31/16
623/1.42

FOREIGN PATENT DOCUMENTS

WO    WO-2016148648 A1 *    9/2016    ............... A61F 2/04

OTHER PUBLICATIONS

"Evaluation of electrospun PLLA/PEGDMA polymer coatings for vascular stent material" Boodagh, Parnaz ; Guo, Dong-Jie ; Nagiah, Naveen ; Tan, Wei Journal of biomaterials science. Polymer ed., 2016, vol. 27 (11), p. 1086-1099.*

(Continued)

*Primary Examiner* — Javier G Blanco
(74) *Attorney, Agent, or Firm* — Medlen & Carroll, LLP

(57) ABSTRACT

The present invention relates to a medical implant, and more particularly, to a vascular implant having a dual coating structure for preventing in-stent restenosis and thrombosis. In one embodiment, the invention contemplates a vascular stent with a coating comprising a hydrophobic, degradable core with a coaxial sheath comprising at least one polyethylene-glycol derivative. In one embodiment, the at least one polyethylene-glycol derivative comprises polyethylene-glycol dimethacrylate.

11 Claims, 27 Drawing Sheets

(52) U.S. Cl.
CPC ..... *A61L 2300/416* (2013.01); *A61L 2300/42* (2013.01); *A61L 2300/604* (2013.01); *A61L 2300/606* (2013.01); *A61L 2400/12* (2013.01); *A61L 2420/02* (2013.01); *A61L 2430/20* (2013.01)

(56) References Cited

OTHER PUBLICATIONS

Bäckström, S. et al. (2012) "Tailoring Properties of Biocompatible PEG-DMA Hydrogels with UV Light," Material Science and Applications 3(6), 425-431.
Boodagh, P. (2017) Evaluation of Fibrous Polymeric Coating over Vascular Stent Material, in *Department of Civil, Environmental and Architectural Engineering*, University of Colorado Boulder,.
Boodagh, P. et al. (2016) "Evaluation of electrospun PLLA/PEGDMA polymer coatings for vascular stent material," *Journal of Biomaterials Science, Polymer Edition* 27(11), 1086-1099.
Brown, B. N. et al. (2010) "Surface Characterization of Extracellular Matrix Scaffolds," *Biomaterials* 31(3), 428-437.
Byfield, F. J. et al. (2009) "Endothelial actin and cell stiffness is modulated by substrate stiffness in 2D and 3D," *Journal of Biomechanics* 42(8), 1114-1119.
Chang, Z. et al. (2018) "Nanomechanics and ultrastructure of the internal mammary artery adventitia in patients with low and high pulse wave velocity," *Acta Biomaterialia* 73, 437-448.
Chen, S. et al. (2010) "Surface hydration: Principles and applications toward low-fouling/nonfouling biomaterials," *Polymer* 51(23), 5283-5293.
Curcio, A. et al. (2011) "Mechanisms of Smooth Muscle Cell Proliferation and Endothelial Regeneration After Vascular Injury and Stenting and Approach to Therapy," *Circulation Journal* 75(6), 1287-1296.
Dahan, N. et al. (2012) "Porcine small diameter arterial extracellular matrix supports endothelium formation and media remodeling forming a promising vascular engineered biograft," *Tissue Engineering Part A* 18(3-4), 411-422.
Duncombe, T. A. et al. (2016) "Hydrogel Pore-Size Modulation for Enhanced Single-Cell Western Blotting," *Advanced Materials* 28(2), 327-334.
Dutov, P. et al. (2016) "Measurement of Elastic Modulus of Collagen Type I Single Fiber," *PLoS One* 11(1), Article No. e0145711.
Farhatnia, Y. et al. (2013) "Evolution of covered stents in the contemporary era: clinical application, materials and manufacturing strategies using nanotechnology," *Biotechnology Advances* 31(5), 524-542.
Fu, W. et al. (2014) "Electrospun gelatin/PCL and collagen/PLCL scaffolds for vascular tissue engineering," *International Journal of Nanomedicine* 9, 2335-2344.
Garg, S. et al. (2010) "Endothelial progenitor cell capture stents: will this technology find its niche in contemporary practice?," *European Heart Journal* 31(9), 1032-1035.
Golecki, H. M. et al. (2014) "Effect of Solvent Evaporation on Fiber Morphology in Rotary Jet Spinning," *Langmuir* 30(44), 13369-13374.
Hamrang, A. et al. (2014) *Foundations of high performance polymers: properties, performance and applications*, Apple Academic Press, ON, Canada.
Inoue, T. et al. (2009) "Molecular Basis of Restenosis and Novel Issues of Drug-Eluting Stents," *Circulation Journal* 73(4), 615-621.
Jia, L. et al. (2013) "Biocompatibility evaluation of protein-incorporated electrospun polyurethane-based scaffolds with smooth muscle cells for vascular tissue engineering," *Journal of Materials Science* 48, 5113-5124.
Khamdaeng, T. et al. (2012) "Arterial stiffness identification of the human carotid artery using the stress-strain relationship in vivo," *Ultrasonics* 52(3), 402-411.

Kohn, J. C. et al. (2016) "Mechanical heterogeneities in the subendothelial matrix develop with age and decrease with exercise," *Journal of Biomechanics* 49(9), 1447-1453.
Ladoux, B. et al. (2017) "Mechanobiology of collective cell behaviours," *Nature Reviews Molecular Cell Biology* 18(12), 743-757.
Li, Y. et al. (2014) "Nanofibers Support Oligodendrocyte Precursor Cell Growth and Function as a Neuron-Free Model for Myelination Study," *Biomacromolecules* 15(1), 319-326.
Liu, C. et al. (2015) "A comparison of centrifugally-spun and electrospun regenerated silk fibroin nanofiber structures and properties," *RSC Advances* 5(119), 98553-98558.
Liu, F. et al. (2016) "Distal vessel stiffening is an early and pivotal mechanobiological regulator of vascular remodeling and pulmonary hypertension," *JCI insight* 1(8), e86987.
Mohomed, K. et al. (2013) "Differential Scanning Calorimetry (DSC) as an Analytical Tool in Plastics Failure Analysis," *American Laboratory* 45(3), 20-23.
Nagiah, N. et al. (2015) "Highly Compliant Vascular Grafts with Gelatin-Sheathed Coaxially Structured Nanofibers," *Langmuir* 31(47), 12993-13002.
Park, J. S. et al. (2007) "Mechanobiology of mesenchymal stem cells and their use in cardiovascular repair," *Frontiers in Bioscience* 12, 5098-5116.
Peloquin, J. et al. (2011) "Indentation measurements of the subendothelial matrix in bovine carotid arteries," *Journal of Biomechanics* 44(5), 815-821.
Sommer, G. et al. (2018) "Mechanical response of human subclavian and iliac arteries to extension, inflation and torsion," *Acta Biomaterialia* 75, 235-252.
Speranza, V. et al. (2014) "Characterization of the Polycaprolactone Melt Crystallization: Complementary Optical Microscopy, DSC, and AFM Studies," *Scientific World Journal* 2014, 9.
Stefanini, G. G. et al. (2013) "Drug-Eluting Coronary-Artery Stents," *New England Journal of Medicine* 368(3), 254-265.
Tze-Man, K. et al. (1993) "Surface characterization and platelet adhesion studies of plasma-sulphonated polyethylene," *Biomaterials* 14(9), 657-664.
Uchida, Y. et al. (2010) "Formation of Web- and Membrane-Like Structures on the Edges of Bare-Metal Coronary Stents," *Circulation Journal* 74(9), 1830-1836.
Vatankhah, E. et al. (2014) "Electrospun tecophilic/gelatin nanofibers with potential for small diameter blood vessel tissue engineering," *Biopolymers* 101(12), 1165-1180.
Vroman, I. et al. (2009) "Biodegradable Polymers," *Materials* 2(2), 307-344.
Wen, J. H. et al. (2014) "Interplay of matrix stiffness and protein tethering in stem cell differentiation," *Nature Materials* 13(10), 979-987.
Wilson, W. M. et al. (2013) "Advances in Coronary Stent Technology: Current Expectations and New Developments," *DovePress* 4, 85-96.
Wingate, K. et al. (2012) "Compressive Elasticity of Three-Dimensional Nanofiber Matrix Directs Mesenchymal Stem Cell Differentiation to Vascular Cells with Endothelial or Smooth Muscle Cell Markers," *Acta Biomaterialia* 8(4), 1440-1449.
Wingate, K. et al. (2014) "Synergism of matrix stiffness and vascular endothelial growth factor on mesenchymal stem cells for vascular endothelial regeneration," *Tissue engineering. Part A* 20(17-18), 2503-2512.
Yeh, C.-C. et al. (2011) "The Effect of Polymer Molecular Weight and UV Radiation on Physical Properties and Bioactivities of PCL Films," *Cellular Polymers* 30(5), 261-276.
Zhao, W. et al. (2013) "Diaphragmatic muscle reconstruction with an aligned electrospun poly(ε-caprolactone)/collagen hybrid scaffold," *Biomaterials* 34(33), 8235-8240.
Zhu, C. et al. (2014) "Characterization of a co-electrospun scaffold of HLC/CS/PLA for vascular tissue engineering," *Bio-medical Materials and Engineerin* 24(6), 1999-2005.
Zilla, P. et al. (2007) "Prosthetic vascular grafts: Wrong models, wrong questions and No. healing," *Biomaterials* 28(34), 5009-5027.

(56) References Cited

OTHER PUBLICATIONS

PCT International Search Report of International Application No. PCT/US2019/039961 dated Nov. 15, 2019.

\* cited by examiner

PRO-HEALING, PRO-REGENERATIVE NANOFIBROUS COATING FOR MEDICAL IMPLANTS

STATEMENT OF GOVERNMENTAL SUPPORT

This invention was made with government support under grant number HL119371 awarded by the National Institutes of Health. The government has certain rights in the invention

FIELD OF THE INVENTION

The present invention relates to a medical implant, and more particularly, to a vascular implant having a dual coating structure for preventing in-stent restenosis and thrombosis.

BACKGROUND OF THE INVENTION

Degradable, hydrophobic polymers like poly 1-lactide acid (PLLA) are often used to coat vascular stents, but they tend to attract platelet and plasma protein adhesion ultimately leading to thrombosis and overgrowth of smooth muscle cells in the stent. Therefore, there is a continued need for a type of coating which avoids the complications of thrombosis and overgrowth of smooth muscle cells with coated materials, such as stents.

SUMMARY OF THE INVENTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The present invention relates to a medical implant, and more particularly, to a vascular implant having a dual coating structure for preventing in-stent restenosis and thrombosis. In one embodiment, the invention contemplates a vascular stent with a coating comprising a hydrophobic, degradable core with a coaxial sheath comprising at least one polyethylene-glycol derivative. In one embodiment, said at least one polyethylene-glycol derivative comprises polyethylene-glycol dimethacrylate. In one embodiment, said at least one polyethylene-glycol derivative comprises polyethylene-glycol modified with thiol-ene. In one embodiment, said at least one polyethylene-glycol derivative comprises polyethylene-glycol modified with hydroxy acid groups. In one embodiment, said hydrophobic, degradable core comprises a poly L-lactide acid core. In one embodiment, said hydrophobic, degradable core comprises a polycaprolactone core. In one embodiment, said hydrophobic, degradable core comprises a polyglycolic acid core. In one embodiment, said hydrophobic, degradable core comprises a poly(lactic-co-glycolic acid) core. In one embodiment, said hydrophobic, degradable core comprises a polyurethane core. In one embodiment, said hydrophobic, degradable core comprises a mixture of at least two of polymers from the group consisting of poly L-lactide acid, polycaprolactone, polyglycolic acid, poly(lactic-co-glycolic acid), and polyurethane. In one embodiment, said coating further comprises a controlled release agent. In one embodiment, said coating further comprises a therapeutic agent. In one embodiment, said therapeutic agent comprises an anti-proliferation agent. In one embodiment, said hydrophobic, degradable core provided controlled drug release. In one embodiment, said sheath integrates a surface signaling mechanism. In one embodiment, said surface signaling mechanism that simultaneously aids in regeneration. In one embodiment, said coating further comprises an interactive surface. In one embodiment, said coating further comprises sub-millimeter scale (such as nanoscale) fibers. In one embodiment, said sub-millimeter scale (such as nanoscale) fibers provide a uniform surface. In one embodiment, said sub-millimeter scale (such as nanoscale) fibers comprise a cell recognition platform. In one embodiment, said coating has no delamination. In one embodiment, said coating has an elastic modulus ranging from 100 to 1000 kPa. In one embodiment, said coating has an elastic modulus ranging from 172 to 729 kPa. In one embodiment, said the elasticity of said polyethylene-glycol dimethacrylate sheath is tunable by varying the photopolymerization time.

In one embodiment, the invention contemplates a method of producing a stent with a coating, said coating comprising a poly L-lactide acid core with a coaxial sheath comprising polyethylene-glycol dimethacrylate comprising: a) providing; i. a stent; ii. poly L-lactide acid; and iii. polyethylene-glycol dimethacrylate; b) combining said poly L-lactide acid and said polyethylene-glycol dimethacrylate under conditions to create a hybrid fiber comprising a poly L-lactide acid core with a coaxial sheath comprising polyethylene-glycol dimethacrylate; c) coating said stent with said hybrid fiber to create a hybrid fiber coating upon said stent; and d) photopolymerizing said hybrid fiber coating. In one embodiment, said conditions to create a hybrid fiber comprising a poly L-lactide acid core with a coaxial sheath comprising polyethylene-glycol dimethacrylate comprises coaxially electrospinning said polymers. In one embodiment, said coating comprises electrospinning said hybrid fiber upon said stent.

In one embodiment, the invention contemplates a vascular stent with a coating comprising a poly L-lactide acid core with a coaxial sheath comprising polyethylene-glycol dimethacrylate. In one embodiment, said coating has an elastic modulus ranging from 100 to 1000 kPa. In one embodiment, said coating has an elastic modulus ranging from 172 to 729 kPa. In one embodiment, said the elasticity of said polyethylene-glycol dimethacrylate sheath is tunable by varying the photopolymerization time.

In one embodiment, the invention contemplates a method of producing a stent with a coating, said coating comprising a poly L-lactide acid core with a coaxial sheath comprising polyethylene-glycol dimethacrylate comprising: a. providing; i. a stent; ii. poly L-lactide acid; and iii. polyethylene-glycol dimethacrylate; b. combining said poly L-lactide acid and said polyethylene-glycol dimethacrylate under conditions to create a hybrid fiber comprising a poly L-lactide acid core with a coaxial sheath comprising polyethylene-glycol dimethacrylate; c. coating said stent with said hybrid fiber to create a hybrid fiber coating upon said stent; and d. photo-polymerizing said hybrid fiber coating. In one embodiment, said conditions to create a hybrid fiber comprising a poly L-lactide acid core with a coaxial sheath comprising polyethylene-glycol dimethacrylate comprises coaxially electrospinning said polymers. In one embodiment, said coating comprises electrospinning said hybrid fiber upon said stent.

In one embodiment, the invention contemplates a medical implant with a coating comprising a hydrophobic, degradable core with a coaxial sheath comprising at least one polyethylene-glycol derivative. In one embodiment, said at least one polyethylene-glycol derivative comprises polyethylene-glycol dimethacrylate. In one embodiment, said at least one polyethylene-glycol derivative comprises polyethylene-glycol modified with thiol-ene. In one embodiment, said at least one polyethylene-glycol derivative comprises polyethylene-glycol modified with hydroxy acid groups. In one embodiment, said hydrophobic, degradable core comprises a poly L-lactide acid core. In one embodiment, said hydrophobic, degradable core comprises a polycaprolactone core. In one embodiment, said hydrophobic, degradable core comprises a polyglycolic acid core. In one embodiment, said hydrophobic, degradable core comprises a poly(lactic-co-glycolic acid) core. In one embodiment, said hydrophobic, degradable core comprises a polyurethane core. In one embodiment, said hydrophobic, degradable core comprises a mixture of at least two of polymers from the group consisting of poly L-lactide acid, polycaprolactone, polyglycolic acid, poly(lactic-co-glycolic acid), and polyurethane. In one embodiment, said medical implant comprises a soft tissue implant. In one embodiment, said medical implant comprises a tissue-regenerative implant. In one embodiment, said medical implant comprises a cardiovascular implant. In one embodiment, said cardiovascular implant is selected from the group consisting of vascular stent, vascular graft, and heart valve. In one embodiment, said cardiovascular implant is selected from the group consisting of vascular graft, heart valve, cardiovascular implants, and tissue-regenerative implant. In one embodiment, said coating further comprises a controlled release agent. In one embodiment, said coating further comprises a therapeutic agent. In one embodiment, said therapeutic agent comprises an anti-proliferation agent. In one embodiment, said hydrophobic, degradable core provided controlled drug release. In one embodiment, said sheath integrates a surface signaling mechanism. In one embodiment, said surface signaling mechanism that simultaneously aids in regeneration. In one embodiment, said coating further comprises an interactive surface. In one embodiment, said coating further comprises sub-millimeter scale (such as nanoscale) fibers. In one embodiment, said sub-millimeter scale (such as nanoscale) fibers provide a uniform surface. In one embodiment, said sub-millimeter scale (such as nanoscale) fibers comprise a cell recognition platform. In one embodiment, said coating has no delaminiation. In one embodiment, said coating has an elastic modulus ranging from 100 to 1000 kPa. In one embodiment, said coating has an elastic modulus ranging from 172 to 729 kPa. In one embodiment, said the elasticity of said polyethylene-glycol dimethacrylate sheath is tunable by varying the photopolymerization time.

In one embodiment, the invention contemplates a method of producing a medical implant with a coating, said coating comprising a hydrophobic, degradable polymer core with a coaxial sheath comprising at least one polyethylene-glycol derivative. comprising: a) providing; i. a medical implant; ii. poly L-lactide acid; and iii. polyethylene-glycol dimethacrylate; b) combining said poly L-lactide acid and said polyethylene-glycol dimethacrylate under conditions to create a hybrid fiber comprising a poly L-lactide acid core with a coaxial sheath comprising polyethylene-glycol dimethacrylate; c) coating said medical implant with said hybrid fiber to create a hybrid fiber coating upon said medical implant; and d) photo-polymerizing said hybrid fiber coating. In one embodiment, said conditions to create a hybrid fiber comprising a poly L-lactide acid core with a coaxial sheath comprising polyethylene-glycol dimethacrylate comprises coaxially electrospinning said polymers. In one embodiment, said coating comprises electrospinning said hybrid fiber upon said medical implant. In one embodiment, said at least one polyethylene-glycol derivative comprises polyethylene-glycol dimethacrylate. In one embodiment, said at least one polyethylene-glycol derivative comprises polyethylene-glycol modified with thiol-ene. In one embodiment, said at least one polyethylene-glycol derivative comprises polyethylene-glycol modified with hydroxy acid groups. In one embodiment, said hydrophobic, degradable core comprises a poly L-lactide acid core. In one embodiment, said hydrophobic, degradable core comprises a polycaprolactone core. In one embodiment, said hydrophobic, degradable core comprises a polyglycolic acid core. In one embodiment, said hydrophobic, degradable core comprises a poly(lactic-co-glycolic acid) core. In one embodiment, said hydrophobic, degradable core comprises a polyurethane core. In one embodiment, said hydrophobic, degradable core comprises a mixture of at least two of polymers from the group consisting of poly L-lactide acid, polycaprolactone, polyglycolic acid, poly(lactic-co-glycolic acid), and polyurethane. In one embodiment, said medical implant comprises a tissue-regenerative implant. In one embodiment, said cardiovascular implant is selected from the group consisting of vascular graft, heart valve, cardiovascular implants, and tissue-regenerative implant. In one embodiment, said medical implant comprises a soft tissue implant. In one embodiment, said medical implant comprises a cardiovascular implant. In one embodiment, said cardiovascular implant is selected from the group consisting of vascular stent, vascular graft, and heart valve.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "poly 1-lactide acid" is used throughout to describe a biodegradable polymer for medical device and pharmaceutical applications.

As used herein, the term "polyethylene-glycol dimethacrylate" is used throughout to describe a polymer with the structure:

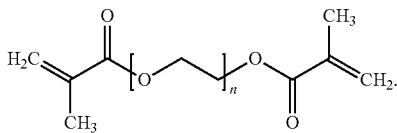

As used herein, the term "anti-proliferation agent" is used throughout to describe a substance which prevents replication (cell division) or growth of cells.

As used herein, the term "surface signaling mechanism" is used throughout to describe surface regulation/modulation of one or more cellular activities.

As used herein, the term "interactive surface" is used throughout to describe a biomimetic surface capable of smartly regulating cell-material interactions on specific target.

As used herein, the term "cell recognition platform" is used throughout to describe extracellular platform capable of regulating specific binding properties.

As used herein, the term "delaminiation" is used throughout to describe separation of layers in a composite structure, with significant loss of mechanical properties.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 2A-F show SEM images showing the fiber structure in the dry state (FIG. 2A-C) or in the hydrated state (FIG. 2D-F), for different UV photopolymerization times including 2 min (FIG. 2A, FIG. 2D), 15 min (FIG. 2B, FIG. 2E), and 60 min (FIG. 2C, FIG. 2F). FIG. 2G shows a comparison of the coaxial PLLA/PEGDMA fiber diameter in dry and hydrated states. FIG. 2H shows TEM image of PLLA/PEGDMA coaxial fiber.

FIG. 3A-E shows representative electron microscopy images and quantitative analyses of coaxially-structured fibers. FIG. 3A shows TEM images of as-spun coaxial fibers. FIG. 3C shows fiber diameter before and after hydration of coaxial blends. '*' comparing vs. dry, '#' comparing vs. wet high UV dose. FIG. 3 D shows porosity and (E) pore size of coaxial blends before and after hydration. '*' comparing vs. dry PCL/PEG-NB. The coaxial microfibers include: PCL/PEG-NB 5 k and PCL/PEG-NB 10 k. (FIG. 3A) Scale bar=2 μm.

FIG. 4A shows TEM image of discontinuous coaxial fibers. Scale bar=2 FIG. 4B shows SEM image of PCL fibers. Scale bar=10 FIG. 4C shows fiber diameter before and after hydration of coaxial blends from optical imaging. '*' comparing vs. dry, '#' comparing vs. wet high UV dose.

FIG. 5A shows dry samples after UV light polymerization.

FIG. 8A shows a representative stress-strain curves of coaxial PCL/PEG-NB fiber scaffolds polymerized with high UV dose, which are compared with the PCL fiber scaffold. FIG. 8B shows a representative strain sweep results of G' and G", from the rheometer measurements of PCL/PEG-NB 10 k. FIG. 8C shows storage modulus, G', of coaxial fiber scaffolds with PEG-NB 5 k or 10 k. '*': comparing vs. low UV dose.

FIG. 13A shows elastic modulus results from tensile test for samples with different UV photopolymerization times. FIG. 13B shows representative tensile stress-strain curves. FIG. 13C shows storage modulus results from rheometer test for samples with different UV photopolymerization times. FIG. 13D shows complex modulus. "*" denotes significant difference of the denoted column from all the others with $p<0.05$.

FIG. 15A shows elastic modulus results from tensile test for samples with different UV photopolymerization times.

Figure 16:
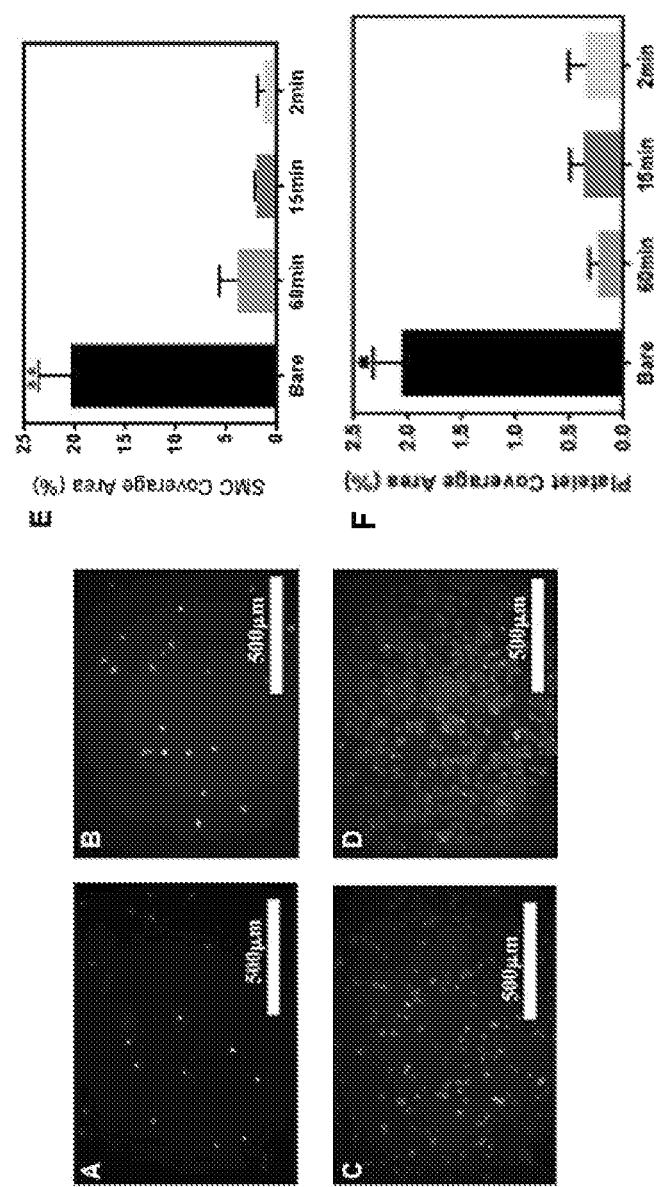
FIG. 16A-D show fluorescent images showing the attachment of SMCs stained with F-actin (green) and DAPI (blue) on nitinol pieces coated with coaxial PCL-PEGDMA fibers with different UV photopolymerization times, including 2 min (FIG. 16A), 15 min (FIG. 16B), and 60 min (FIG. 16C), as well as on a bare nitinol piece (FIG. 16D).

FIG. 16E shows comparisons of the SMC attachment area ratios. "**": denotes significant difference of the denoted column from all others with p<0.05.

FIG. 16F shows comparisons of the platelet attachment area ratios. "*": denotes significant difference of the denoted column from all others with p<0.05

Figure 17:
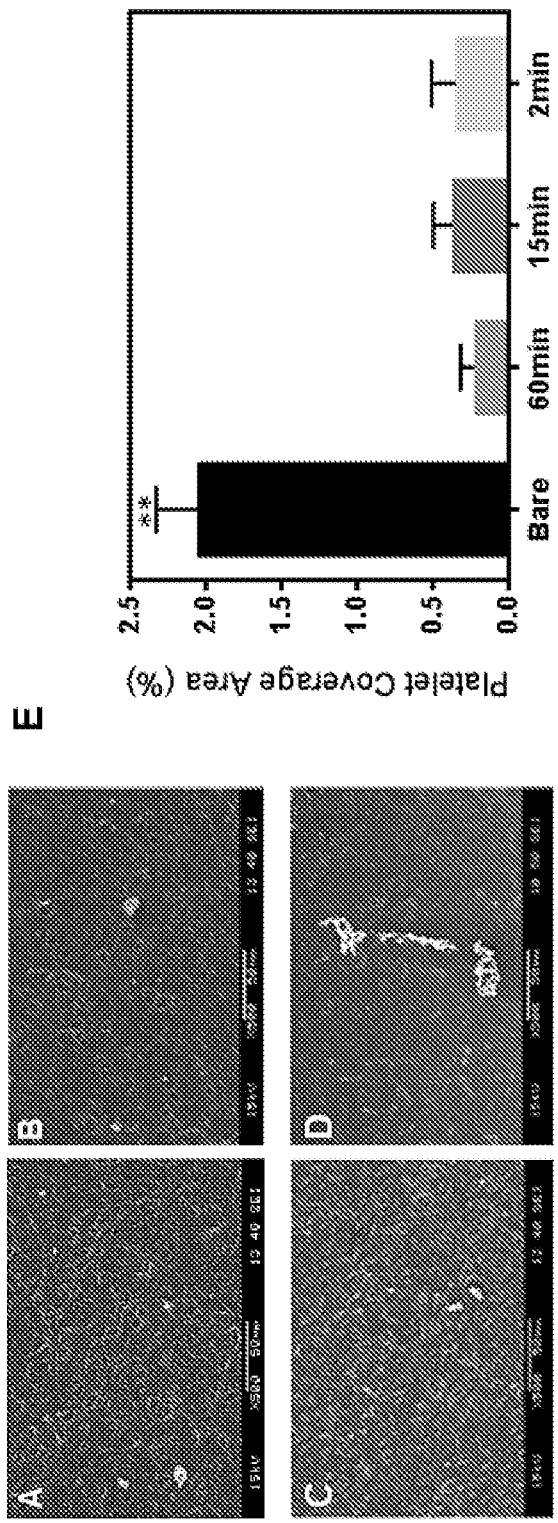

FIG. 17A-D shows SEM images showing the adhesion of platelets on nitinol pieces coated with coaxial PCL-PEGDMA fibers with different UV photopolymerization times, including 2 min (FIG. 17A), 15 min (FIG. 17B), and 60 min (FIG. 17C), as well as on a bare nitinol piece (FIG. 17D).

FIG. 17E shows Comparisons of the platelet attachment area ratios. "**": denotes significant difference of the denoted column from all others with p<0.05.

Figure 18:
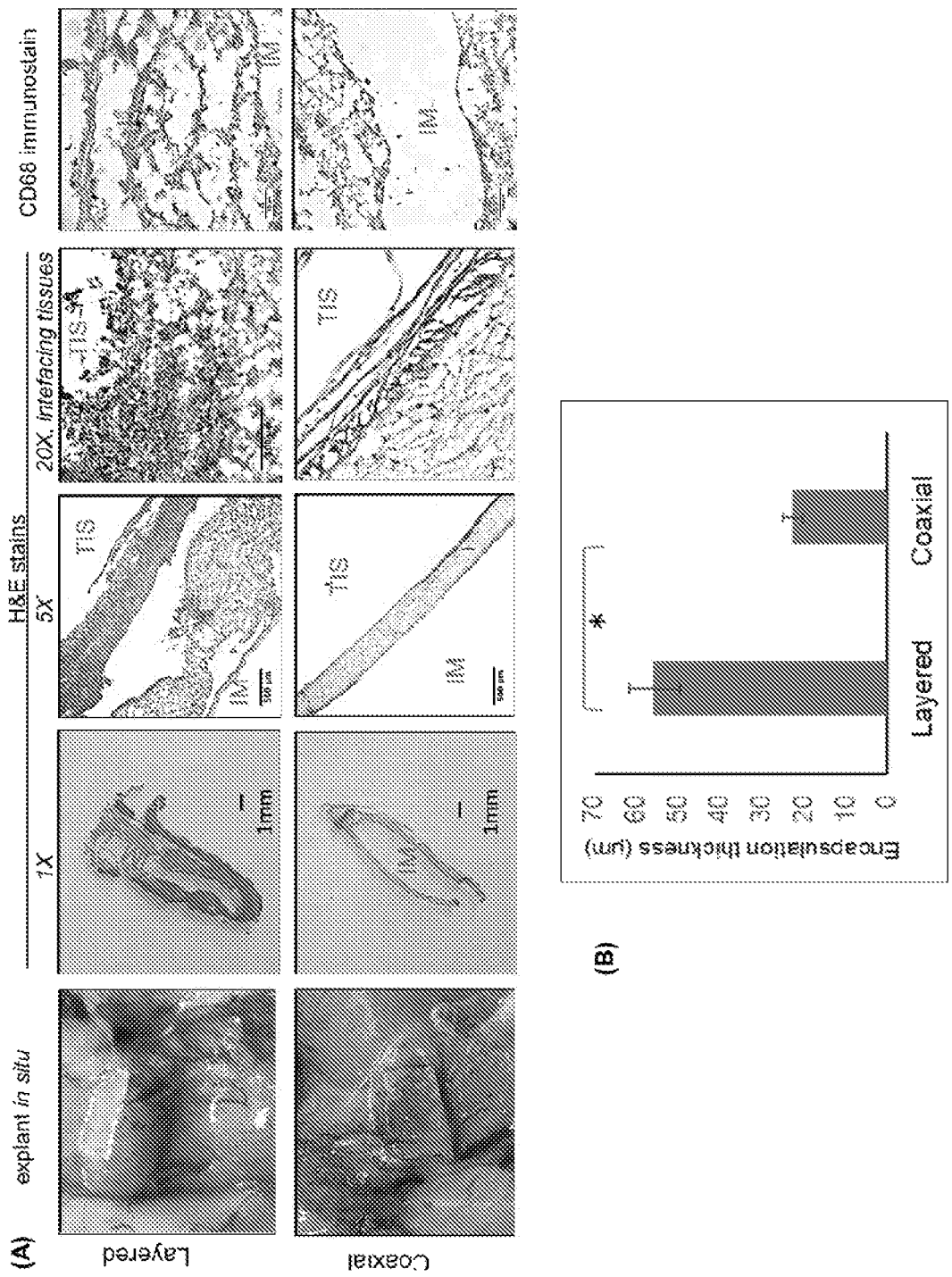

FIG. 18A&B show morphological, histological and inflammatory characteristics of explants after 7 days of implantation: FIG. 18A shows the appearance of explant, as well as H&E stain and CD68 (universal marker for macrophage lineage) immunohistochemistry stain of the encapsulation around explants with their surfaces coated by either bilayered fibers or coaxially-structured fibers; FIG. 18B shows quantitative comparisons of the encapsulation tissue thickness between coaxial fiber and layered materials. Four samples of each type were implanted and analyzed. "*" shows p<0.05. "IM" shows the implant location, while "TIS" shows interfaces with neighboring tissues.

Figure 19:
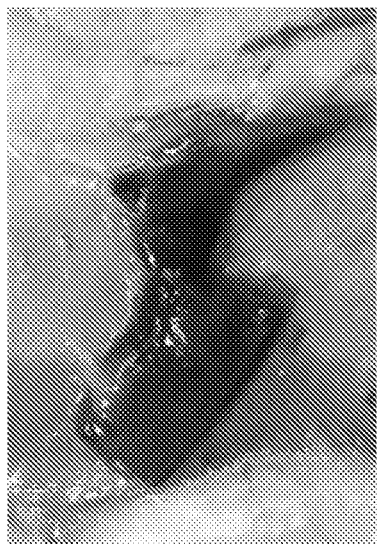

FIG. 19 shows explant appearance of bare metal materials after 7 days of implantation.

Figure 20:
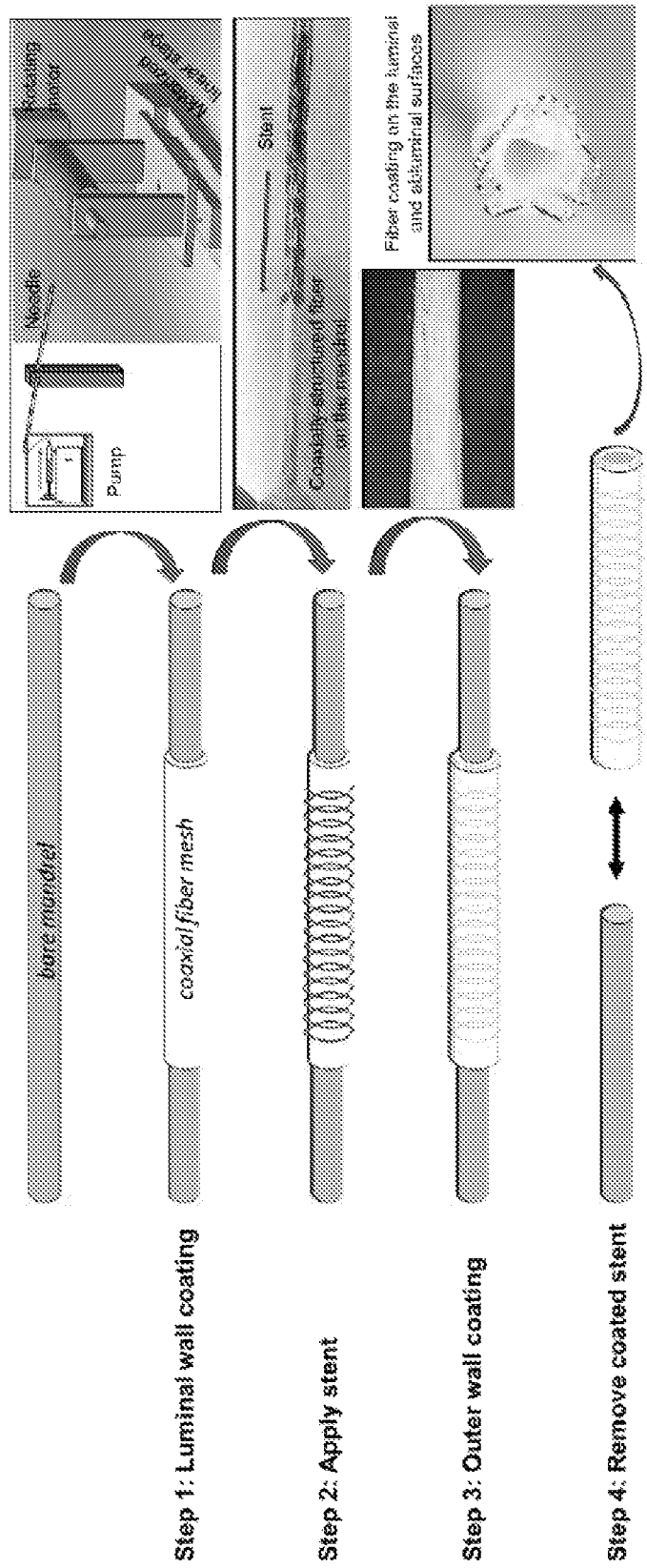

FIG. 20 show an illustration of one embodiment of a fabrication process and outcome for a small-diameter vascular stent coated with coaxially-structured PLLAPEGDMA fibers. The approach involve using fiber-coated mandrel to carry the stent as fiber collector. Resultant stent devices, as shown with representative cross-sectional and longitudinal view images, exhibit uniform fibrous coatings in the lumen and over the abluminal surface.

Figure 21:
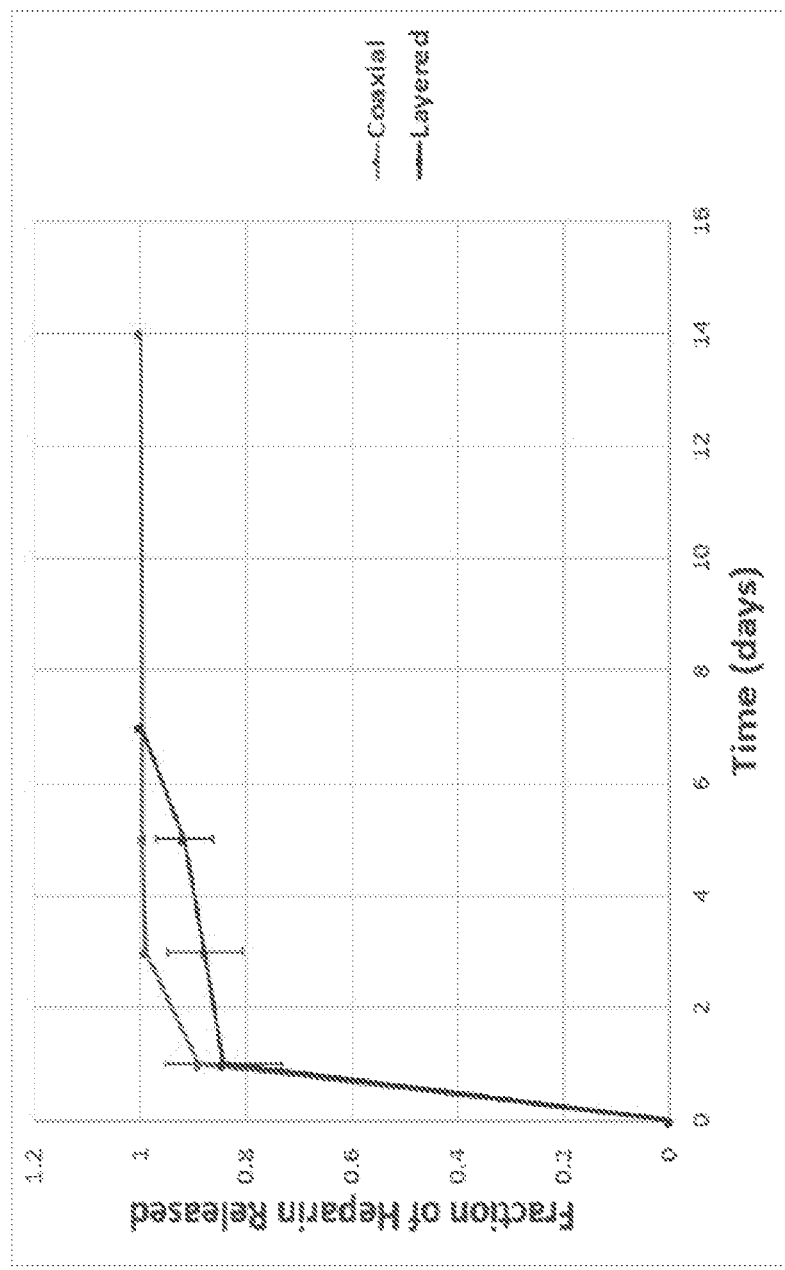

FIG. 21 shows Results from heparin release assay for both coaxial and layered samples over 14 days. Error bars represent standard deviation. The opportunity for biomolecule impregnation and drug release from the coaxially structured materials was shown with heparin release assay. Both coaxial and layered tubular structures (ID=1.5 mm) were used in the assay. Heparin was added to the PLLA solution for each sample type. The collected solution samples were analyzed using a Biophen Heparin Anti-Xa analysis kit.

Figure 22:
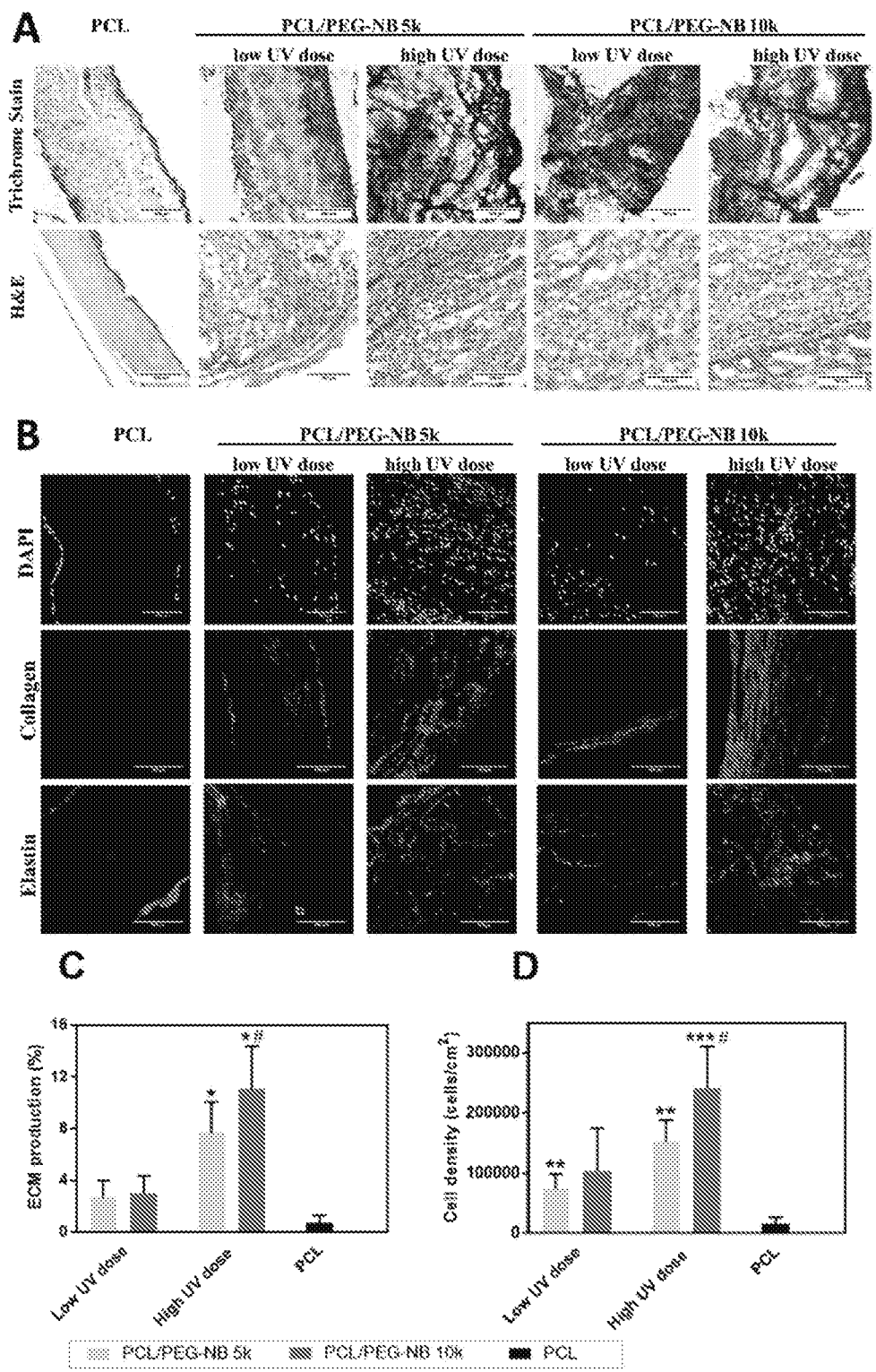

FIG. 22A-D show the biocompatibility of the explanted scaffolds. FIG. 22A shows histological analysis results, showing infiltrated cells and deposited ECM in the explanted scaffolds. Masson's trichrome stain shows collagen and mucus in blue, nuclei in black, and cytoplasm, keratin, muscle, and intercellular fiber in red. Collagen deposition is observed in the high UV dose coaxial scaffolds. H&E stain shows a large number of cells recruited in the coaxial material compared to PCL fibers, as well as in the high UV dose coaxial scaffolds compared to the low UV dose scaffolds and PCL fibers. FIG. 22B shows two-photon imaging of the explanted scaffolds. Images show the infiltrated cells (DAPI stain of cell nuclei), as well as the newly-synthesized collagen (red, from SHG imaging) and elastin (green, from TPE imaging). High UV dose coaxial scaffolds show a large number of infiltrated cells as well as an increased deposition of collagen and elastin compared to the other scaffolds. FIG. 22C shows the ECM production and FIG. 22D shows cell density in the explanted scaffolds. High UV dose increased both cell density and ECM production in the coaxial fiber scaffolds compared to PCL fibers. comparing vs PCL, '#' comparing vs. PCL/PEG-NB 10 k with low UV dose. (A-B) scale bar=100 μm.

Figure 23:
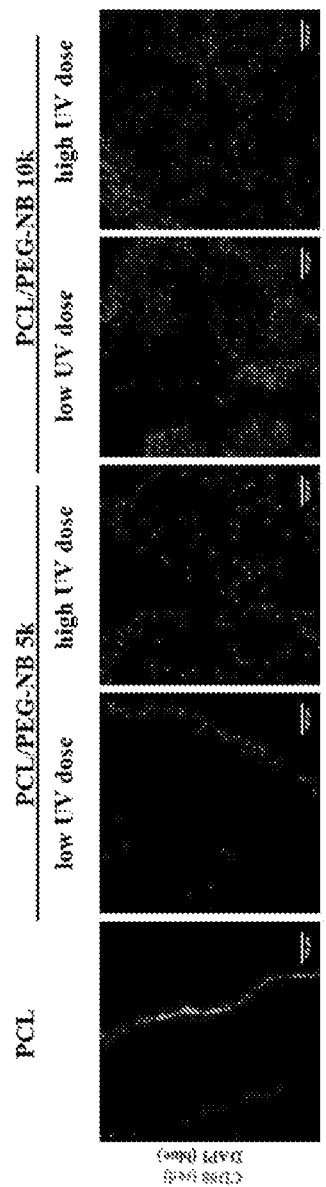

FIG. 23 shows an evaluation of macrophage presence on the five explanted fiber scaffolds. Fluorescent microscopy images from immunofluorescent staining show CD68 (red) indicating macrophages, and DAPI (blue) indicating cell nuclei. Results demonstrate no macrophage presence in the coaxial scaffolds while some macrophages are detected in the PCL scaffolds. Images were taken at 20×. Scale bars=100 μm.

Figure 24:
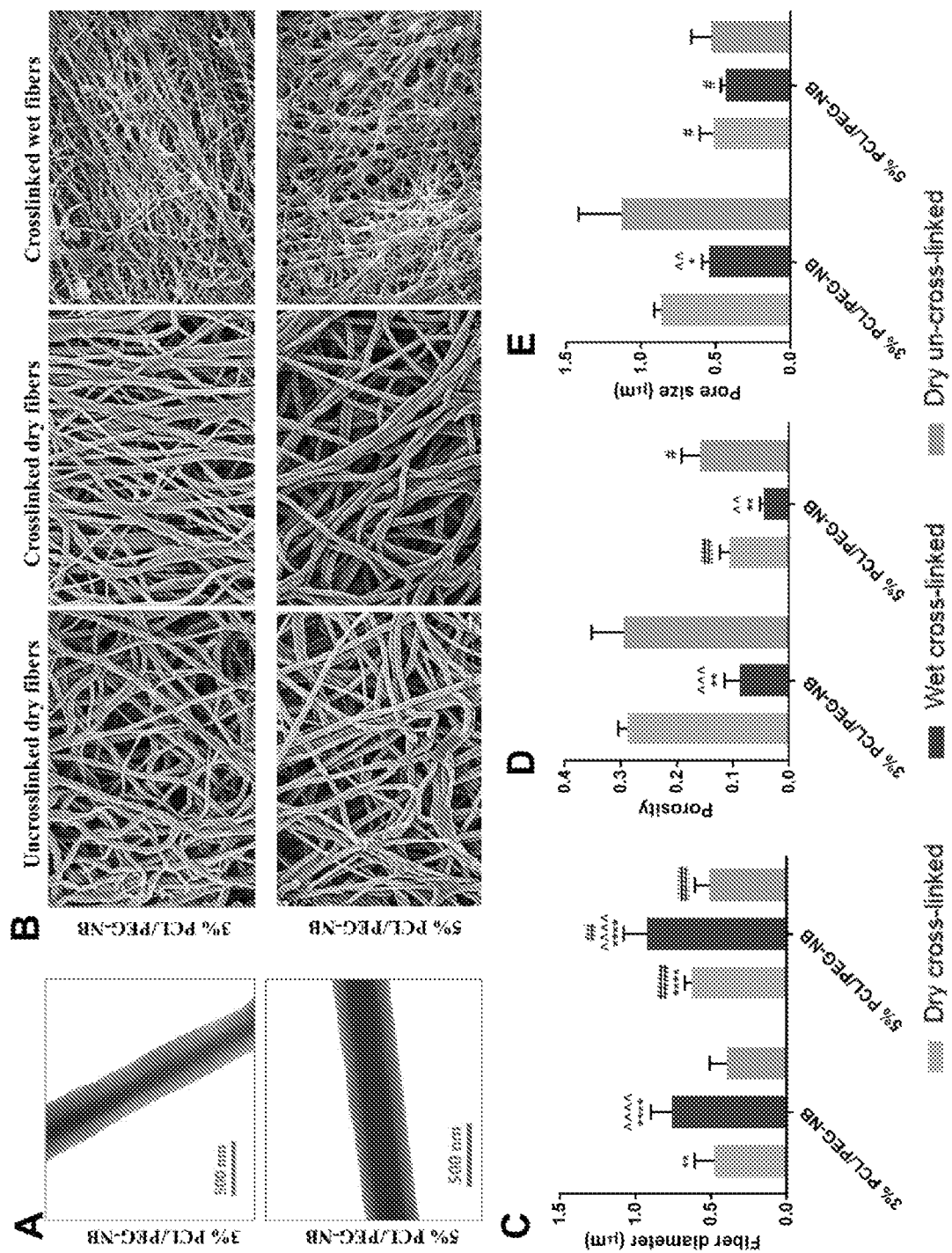

FIG. 24A-E shows representative electron microscopy images and quantitative analyses of coaxially-structured fibers. FIG. 24A shows TEM images of as-spun coaxial fibers. FIG. 24B shows SEM images of the uncrosslinked and crosslinked coaxial fiber scaffolds, which were stored in either dry or hydrated conditions. FIG. 24C shows Fiber diameter of the uncrosslinked and crosslinked coaxial blends, before and after hydration. FIG. 24D shows porosity and FIG. 24E pore size of the uncrosslinked and crosslinked coaxial blends, before and after hydration. '*' comparing vs. dry uncrosslinked, '^' comparing vs. dry crosslinked, '#' comparing vs. 3% PCL/PEG-NB. Significance levels were set at: *P<0.05; P<0.01; *P<0.001; ****P<0.0001. Scale bar: (FIG. 24A) 500 nm. (FIG. 24B) 10 μm.

Figure 25:
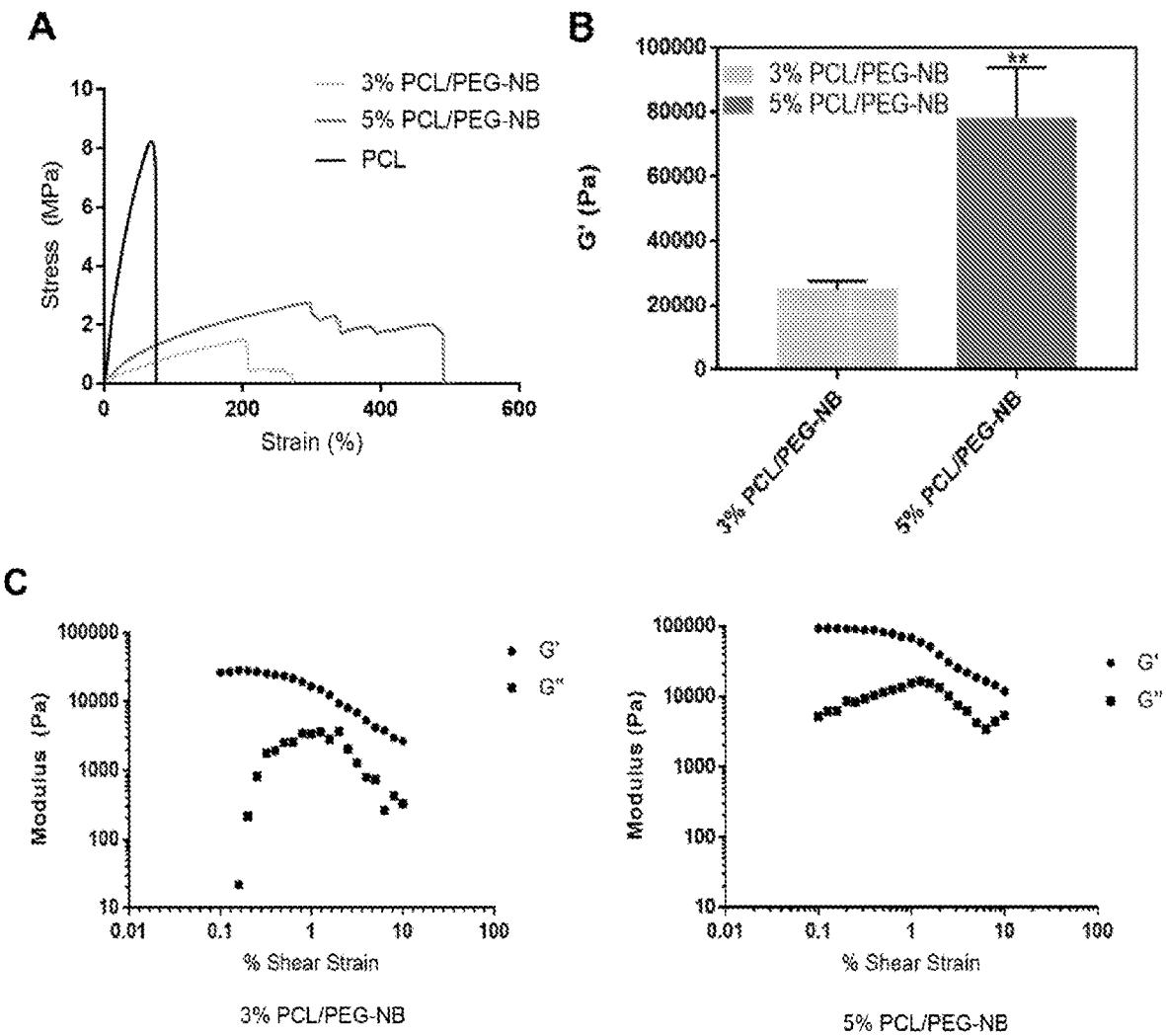

FIG. 25A-C shows tensile and viscoelastic properties of PCL/PEG-NB coaxially-structured fibrous scaffolds. FIG. 25A shows representative stress-strain curves of coaxial 3% and 5% PCL/PEG-NB fiber scaffolds, which are compared with the PCL fiber scaffold. FIG. 25B shows storage modulus, G', of coaxial fiber scaffolds with 3% or 5% PCL/PEG-NB. '*': comparing vs. 3% PCL/PEG-NB. FIG. 25C shows representative strain sweep results of G' and G", from the rheometer measurements of 3% and 5% PCL/PEG-NB.

Figure 26:
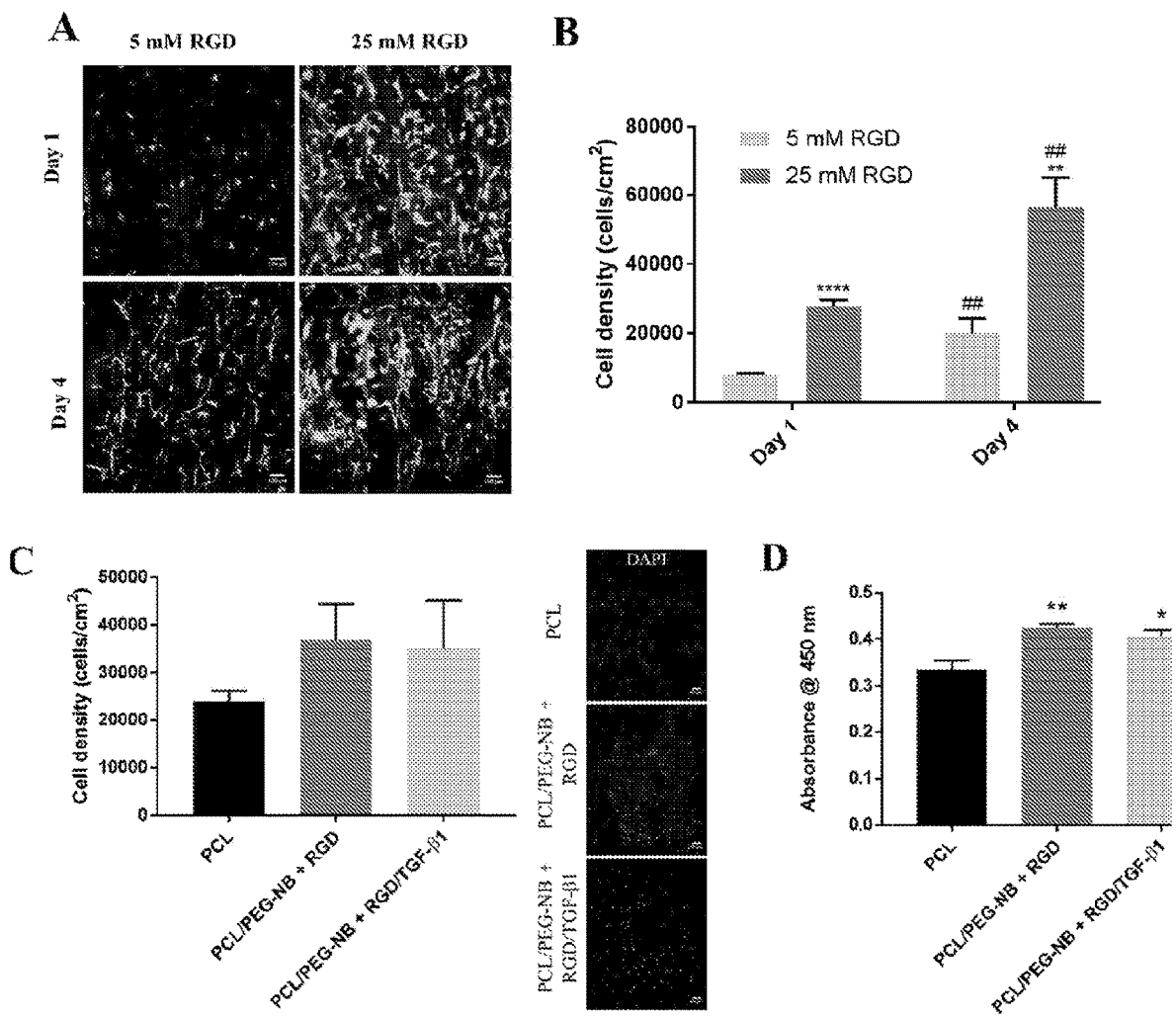

FIG. 26A-D shows cell compatibility of the coaxial fiber grafts. FIG. 26A shows In vitro evaluation of hMSC attachment (day 1) and proliferation (day 4) on the coaxial fiber scaffolds, assessing different RGD concentrations. Fluorescent microscopy images show F-actin (green) stain in hMSCs cultured for 24 h and 96 h on the scaffolds composed of PCL/PEG-NB. Results demonstrate preferential cell attachment and proliferation on the scaffold treated with 25 mM RGD. Images were taken at 10×. Scale bars=100 μm. FIG. 26B shows cell density on coaxial scaffolds treated with different RGD concentrations, measured at day 1 and day 4. '*': comparing vs. 5 mM, '#': comparing vs. day 1. FIG. 26C shows cell density on PCL/PEG-NB scaffolds functionalized with both RGD or RGD+TGF-β1, as well as PCL fiber scaffold, measured at day 4. FIG. 26D shows CCK assay of the cell cultures on the coaxial fiber scaffolds demonstrating higher viability of cells cultured on the coaxial scaffolds compared to PCL. The absorbances were taken at 450 nm 96 h after cell seeding. '*': comparing vs. PCL.

Figure 27:
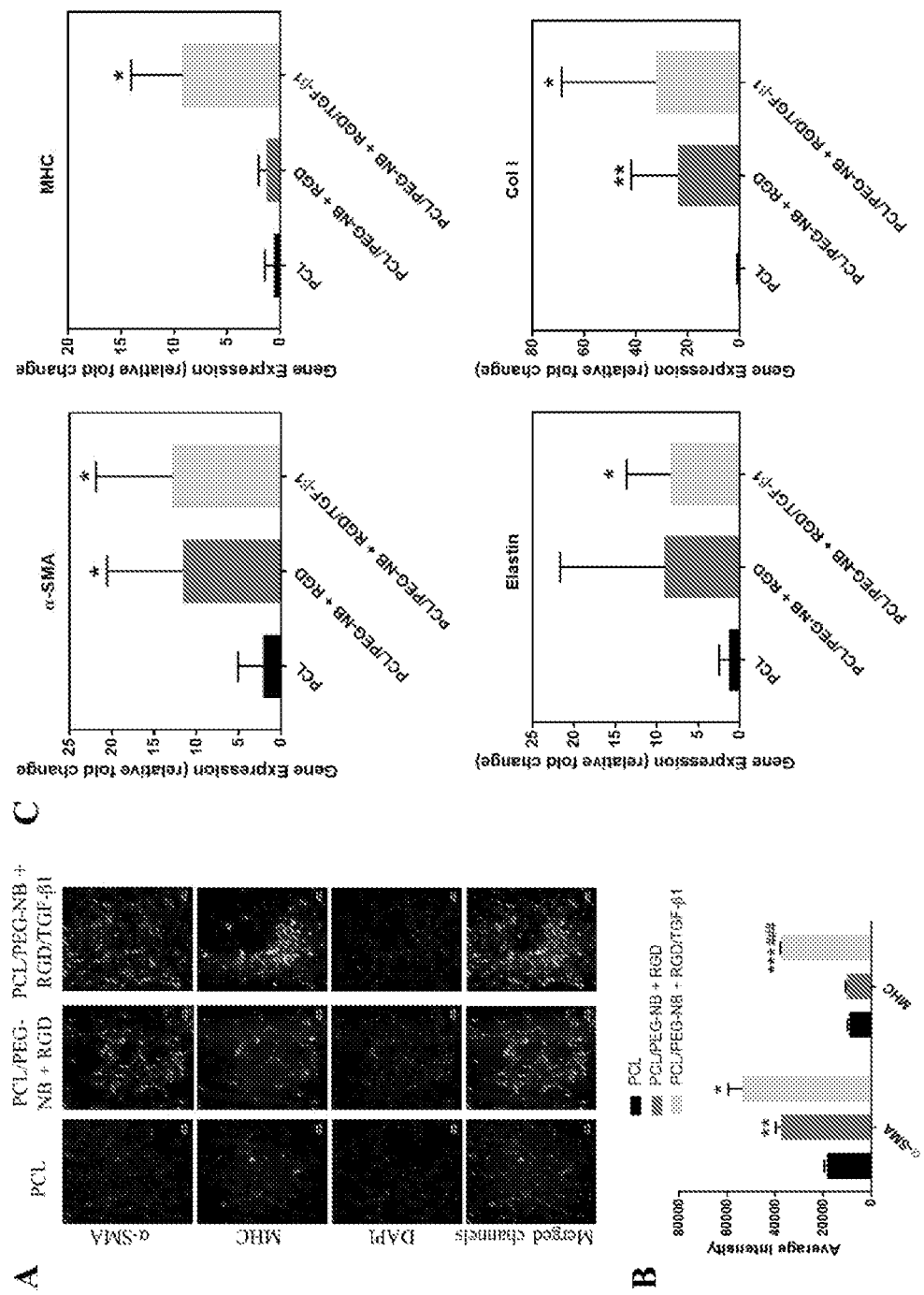

FIG. 27A-C shows cell differentiation in the coaxial fiber vascular grafts. FIG. 27A shows confocal microscopy images showing α-SMA and MHC stains in hMSCs cultured for 6 days on scaffolds composed of PCL fibers, PCL/PEG-NB+RGD, and PCL/PEG-NB+RGD/TGF-β1. DAPI stain (blue) is shown as well. Images were taken at 10×. Scale bars=50 μm. FIG. 27B shows the average intensity calculated as total mean grey value divided by total number of cells from confocal images of the scaffolds. '*' comparing vs. PCL, '#' comparing vs. PCL/PEG-NB+RGD. FIG. 27C

DETAILED DESCRIPTION OF THE INVENTION

The present invention relates to a medical implant, and more particularly, to a vascular implant having a dual coating structure for preventing in-stent restenosis and thrombosis.

Degradable, hydrophobic polymers like poly 1-lactide acid (PLLA) are often used to coat vascular stents, but they tend to attract platelet and plasma protein adhesion ultimately leading to thrombosis and overgrowth of smooth muscle cells in the stent. The present invention reports the development of novel stent coating materials made of nanostructured hybrid fibers including a hydrophilic polyethylene-glycol dimethacrylate (PEGDMA) sheath that coaxially covers a hydrophobic PLLA core. Attenuated total reflection-Fourier transformed infrared spectroscopy and transmission electron microscopy imaging demonstrated the PEGDMA sheath coaxially wrapping the PLLA core. The PEGDMA/PLLA coating exhibited gel-like features with a high water content and soft surface, and possessed high mechanical strength with an elastic modulus ranging from 172 to 729 kPa. The novel mechanical behaviors, arising from the hierarchical interfaces of nanostructured hybrid composite fibers, simulate those of vascular tissues which possess overall structural strength to withstand mechanical forces and microscale softness to offer hydrated and elastic cell environments. The elasticity of the hydrophilic PEGDMA sheath are tunable by the photopolymerization time with shorter time yielding softer coating. Three photopolymerization times for PEGDMA/PLLA coatings were examined. Scanning electron microscopy images showed similar, uniform fibrous structures in all coatings. Importantly, all the PEGDMA/PLLA coatings strongly reduced SMC overgrowth and discouraged platelet adhesion and activation, when compared to the bare nitinol stent surface. The anti-thrombotic, anti-proliferative features likely arise from the non-adhesive nature of hydrophilic PEGDMA sheath. The nanostructured PEGDMA/PLLA fibrous coatings synergizing the advantages of two polymers may be used to improve the performance of vascular implants.

1. Introduction

Cardiovascular disease has been the leading cause of death and morbidity in many developed countries. Among cardiovascular diseases, atherosclerosis, the narrowing of the vessel lumen due to fatty plaque buildup inside arteries, is the most common disease condition. To treat such cardiovascular condition, the stenting method is often used, and it has undergone significant advancement over the past few decades, in particular with the emergence of various stent coatings to elute drugs or to capture endothelial progenitor cells [1-3]. However, the artery stent, such as coronary stent implanted through percutaneous coronary intervention, is associated with two major complications: (a) in-stent thrombosis which leads to thrombotic occlusion, and (b) in-stent restenosis which decreases arterial lumen space due to neointimal proliferation [3]. Thrombosis results from the accumulation of blood components such as platelets and fibrin around the injured blood vessel, whereas restenosis results mainly from abnormal overgrowth of smooth muscle cells (SMCs) around stent struts [4, 5]. It is well known that the composition, structure, and elasticity of the extra-cellular matrix (ECM) can regulate protein adhesion and cell attachment, proliferation, migration, or differentiation. Therefore, identifying key environmental factors that inhibit platelet adhesion and SMC growth is critical for the improvement of artery stents and other cardiovascular implants.

Recent studies have highlighted the influence of mechanical properties of ECM on cellular behaviors, such as cell-matrix adhesions, motility, differentiation, and viability [6, 7]. Emerging evidence supports the hypothesis that cells sense their mechanical environments and amend their behaviors in response to local changes in the matrix stiffness. ECM stiffness can be modulated by a wide array of methods including varying chemical cross-linking, hydrogel density, and scaffold composition [8-10]. Replicating the elasticity of the vessel basement membrane and medial layers in vitro could produce an engineered environment to articulate the in-vivo bio-response. For soft tissues like blood vessels, nanofibers with low elasticity (i.e. in the range of 2-15 kPa) are needed [11]. Recent studies have accentuated the significance of the microenvironment elasticity on cell function [12, 13], mostly focus on muscle, neural or bone tissues [14]. However, little has been done to translate these important environmental controls into the design of vascular implants.

Among the artificial materials used for biomedical applications, biocompatible and biodegradable hydrophobic polymers such as poly L-lactic acid (PLLA) have been favorably used in tissue engineering applications [15-17]. It has also been often used as the material for controlled drug release on drug-eluting stents. In spite of the high mechanical stability, hydrophobic nature of PLLA tend to trigger platelet and plasma protein adhesion, causing platelet aggregation and intimal hyperplasia of the artificial blood vessels [18]. By contrast, polyethylene glycol dimethacrylate (PEGDMA) is a well-recognized non-toxic and bioinert polymer hydrogel, has been widely used as a coating material due to its compatibility with biological system while low protein, cell, and bacterial adhesion on surfaces. PEGDMA is very hydrophilic, which plays an important role in its blood compatibility. Therefore, the combination of hydrophobic polymer of PLLA with hydrophilic PEGDMA may provide appropriate material strength and elasticity with anti-thrombotic and anti-proliferative properties for vascular implants. Material design efforts should be taken to integrate them so that the stiff PLLA core could provide the mechanical strength and stability of the scaffold as well as potential reservoir for drugs while the soft PEGDMA sheath ensures its enhanced anti-thrombosis, anti-proliferation and mimetic viscoelasticity.

To that end, one embodiment of the present invention aims to coaxially electrospin two physically and mechanically different materials into fibers composed of low fouling, non-immunogenic hydrophilic PEGDMA sheathing with the hydrophobic core made of PLLA. These hybrid fibers, as a coating material, might hold potentials for a variety of vascular implant applications. One embodiment of the present invention provides a pathway to control in-stent thrombosis and in-stent restenosis, modulating the activity of platelets and SMCs by designing fiber coating around stent with anticoagulant and anti-proliferative properties. One focus of the present invention is on examining how the elasticity, composition, and structure of fibrous matrix interact to inhibit in-stent thrombosis and in-stent restenosis. Herein, the physical, mechanical, and biological performances of the hybrid fibrous stent coatings are evaluated, using nitinol a widely-used stent material. For this purpose, elasticity of coaxially electrospun coatings was altered by adjusting the UV photopolymerization time. Three UV polymerization times of 2, 15, and 60 min were selected. Mechanical and material characterizations were performed and attachment of platelets and arterial SMCs onto the coatings were assessed in vitro.

2. Materials and Methods 2.1 Materials

All reagents were purchased from Sigma Inc. (St. Louis, Mo.), unless otherwise stated. PEGDMA was synthesized from poly (ethylene glycol) (PEG) which is purchased from Fisher Scientific Inc. (San Francisco, Calif.).

2.2 Preparation of Stent Material and Polymer Coating

In order to simulate stent implant modification in-vitro, nitinol stent materials (Kelloggs research labs, Hudson, N.H.) were used. They were prepared by cutting a nitinol plate with water jet by Waterjet Inc. (Longmont, Colo.) into 5 mm×10 mm pieces. The thickness of each nitinol stent sample was 1 mm. Segments of nitinol were cleaned with the ultrasonic method by first placing the nitinol pieces in an uncapped plastic centrifuge tube filled with acetone for 10 minutes and then with water. After cleaning, the nitinol pieces were treated with oxygen plasma at about 1-2 cm $H_2O$ oxygen pressure for 5 minutes. The activated nitinol pieces were immediately used to collect coaxially electrospun PEGDMA/PLLA polymers. The coated samples were finally placed under UV lamp and allowed photo-polymerization to occur at three different times (2, 15, and 60 min).

2.3 Fabrication of Coaxially Electrospun Fibers

PEGDMA with a molecular weight of 3,000 was synthesized with approximately 90% of the end groups modified with methacrylates as determined by $^1H$ NMR analysis PEGDMA (3000 Da) was synthesized using the method described in previous work [10] with approximately 90% of the end groups modified with methacrylates as determined by $^1H$ NMR analysis.

Electrospinning solution for the core is composed of 3% w/v PLLA dissolved in 2, 2, 2 trifluororethanol (TFE) (Alfa Aesar, Sparks, Nev.). Electrospinning solution for sheath is composed of 50% w/v PEGDMA and 3% w/v polyethylene oxide (PEO, 40 kDa) with mixing volume ratio of 7 and 3, respectively, and 0.4% w/v Irgacure 2959 (12959, 0.6 mg/mL in deionized water; Ciba, Tarrytown, N.Y.) dissolved in TFE. PEGDMA and PEO are hydrophilic polymers dissolvable in water. The reason that water was chosen as the solvent for PEGDMA but TFE for both PLLA and PEGDMA-PEO was to eliminate possible incompatibility problems through coaxial electrospinning of core and sheath. The apparatus used for obtaining coaxial fibers was developed in house. The solution of the core hydrophobic polymer, PLLA, was passed through the inner needle of 22 gauge (0.71 mm in internal diameter), and the sheath PEGDMA-PEO solution was passed through the outer needle of 16 gauge (1.65 mm in internal diameter). A dual syringe holder was used to place the syringes loaded with polymer solutions. This design allows the solutions to be extruded simultaneously. The core and sheath solutions were loaded in 5 ml syringes connected to the positive terminal of a high voltage ES30P 13 W power supply (Gamma High Voltage Research, Ormond Beach, Fla.). The core and sheath polymer solutions were extruded at 0.7 ml/h and 1.1 ml/h, respectively, using syringe pumps (Pump 11 Plus, Harvard Apparatus, Boston, Mass.), and were subjected to an electric potential of 1 kV/cm. The fibers were deposited onto a grounded static aluminum substrate placed at a distance of 17 cm perpendicular to the needle. The coated nitinol specimens with fibrous PLLA/PEGDMA-PEO coating were placed in plastic centrifuge tube under vacuum for 15 min, followed by UV polymerization at 365 nm with an average intensity of 5 mW/cm$^2$ for 2, 15, or 60 min.

For implantation studies, layered fibers made of PLLA fibers and PEGDMA fibers were also fabricated to coat nitinol pieces. Following a protocol modified from our previously established method [10], fibers were prepared by spinning PLLA dissolved in TFE at flow rate of 0.7 mL/h at 8 kV, 8 cm distance from ground for 30 min, and then spinning PEGDMA-PEO at flow rate of 1.1 mL/h at 15 kV voltage, 14 cm distance from ground. All layered prepared samples were polymerized for 60 min.

2.4 Stent Coating Fabrication

A PEO-coated 20 G needle (1.25 mm in diameter) was first attached to an aluminum rod used as a rotating mandrel in the electrospinning system. The needle was then used as the substrate to collect fibers at a rotational speed of 150 rpm for 15 min. Electrospinning setup was established with designated distance, voltage and flow rates with fiber solutions prepared as outlined above. Once coated, the needle was removed from the aluminum rod. Then, a plasma treated vascular stent was carefully slid over the fiber-coated 20 G needle. The needle/stent complex was re-attached to the end of the aluminum rod mandrel. Using the needle/stent complex as the substrate to collect fibers on the mandrel, the electrospinning system ran an additional 20 min following the same parameters as the first step of fiber coating, to allow complete coverage of fibers on the abluminal surface. Upon completion, the coated stent was placed under UV for photo-polymerization, and finally submerged in PBS for 60 min to hydrate the fiber and dissolve the PEO layer for easy removal of the fiber-coated stent from the needle.

2.5 Scanning and Transmission Electron Microscopy Imaging

Samples were then dehydrated through an ethanol series (30, 50, 75, 90, and 100%; 15 min each), and subsequently maintained in 100% ethyl alcohol until drying. They were dried overnight in a vacuum chamber and sputter-coated with gold before scanning electron microscope (SEM) to examine their average diameter. The nitinol substrates coated with the electrospun fibers were mounted on brass stubs and observed under a SEM (JEOL JSM-6480 LV, Peabody, Mass.) operating at an accelerating voltage of 15 kV. The diameters of about 10 different fibers were measured in each of the above case using the Image-J tool to obtain their average diameter. For hydrated state, samples were photopolymerized for 5, 15 and 60 min, and submerged in DI $H_2O$ for 24 h.

Nanostructures of coaxial fibers were observed using H7650 transmission electron microscope (TEM; Hitachi Ltd., Tokyo, Japan) operated at 100 kV to characterize the core-sheath morphology. The coaxiallystructured samples for TEM observation were prepared by directly depositing an ultrathin layer of fibers on carbon-coated copper TEM grids and examined directly.

2.6 Water Contact Angle Measurement

The water contact angle measurement was conducted using GBX Instrument (Bourg de Peage, France) apparatus, which determines the wettability of coaxially electrospun substrate. To start this, a minimal amount (~3 µl) of distilled water droplet was dropped onto the surface of an electrospun mat. The water contact angle was then measured from the image of the droplet.

2.7 Mechanical Testing

Uniaxial tensile testing was performed using electromechanical testing system (MTS Exceed E42, Eden Prairie, Minn.) with 500 N load cell. Samples of coaxially electrospun scaffolds were punched into the dog bone shape with a width of 4 mm and gauge length of 20 mm using ASTM dog-bone D638-V cutter. The samples were secured in the grips of a tensile tester with 15 mm space between grips and loaded until failure. Samples were submerged in DI $H_2O$ for 24 hr before mounted to wedge grips and the tensile testing was performed on them in the hydrated state. Using 150 N load cell, load-elongation measurement was carried out at a speed of 0.03 mm/sec, 25° C. temperature and relative humidity of 65%. Samples with data indicating slip-page or excessive noise were not used. A classic heel-toe stress-strain curve was observed for hydrated coaxial structured electrospun samples. The hydrated elastic modulus of samples was determined from the low-strain linear region (0-25%) of the curve.

The viscoelastic properties of coaxially-spun scaffolds were investigated under shear deformation using an ARES rheometer (TA Instrument, New Castle, Del.). Coaxially electrospun fibers were collected on 3-(trimethoxysilyl)-propyl methacrylate (TMPMA) treated coverslip with 18 mm in diameter and at least 0.3 mm in thickness. Prior to testing, samples were submerged in DI water for 24 hr. Variations in the storage modulus, G', of samples due to increased photopolymerization time were characterized by running a strain sweep at 1 rad/s frequency using a parallel plate configuration rheometer. A vertical load of 16 g was also applied to all samples to prevent slippage. The storage modulus, G', and loss modulus, G", of scaffolds as well as tan δ (where tan δ=G'/G") were determined in the linear viscoelastic region. The complex modulus, G*, can be calculated using $G^*=G'+iG''$. Shear modulus was determined with constant strain application, reflecting the difference in material viscosity. In order to avoid sample slippage during rheometer measurement, the coverslips were treated with TMPMA before electrospun sample deposition. Briefly, coverslips were placed in tube filled with acetone and ultrasound was applied for 45 min. Subsequently, the coverslips were immersed in 70% ethanol for 2-5 minutes, which helped to separate coverslips, and were then dried over kimwipes. After that, they were treated with oxygen plasma for 2 min, and then immediately placed in tubes filled with TMPMA solution (100 ml of 95% ethanol, 3 ml of diluted acetic acid with 1:10 of glacial acetic acid-to-water ratio, and 500 μl of TMPMA). The tubes with coverslips in TMPMA solution were placed over shaker table for 30 min to ensure uniform coating. The coverslips were then rinsed in 95% ethanol twice, dried over kimwipes, and stored at −20° C. freezer or immediately used as the substrate for nanofiber collection.

2.8 ATR-FTIR Spectroscopy

Attenuated total reflection-Fourier transform infrared spectroscopy (ATR-FTIR) measure-ments were carried out on peeled fibrous membranes using Nicolet 5700 FTIR spectrometer (Thermo Fisher Scientific, Logan, Utah) equipped with a diamond ATR crystal. Typically, 30 scans were signal-averaged to reduce spectral noise. The spectrum of the samples ranged from 600 to 4000 $cm^{-1}$.

ATR-FTIR was used to evaluate coaxially electrospun scaffolds for double bond conversion by inspecting the disappearance of the C=C peak occurring at around 1635 $cm^{-1}$ within the acrylate group. Samples with three photo-polymerzation times, 2, 15 and 60 min, were examined with ATR-FTIR. ATR-FTIR spectra were normalized with the C=O peak located in the range of 1650-1726 $cm^{-1}$ in order to render sample background variation as the peak is independent of photopolymerization. Also, ATR-FTIR was used to probe the surface property of samples, hence demonstrating the coaxially structured electrospun fibers. Data were analyzed using "OriginPro" software (Northampton, Mass.).

2.9 Thermogravimetric Analysis

Thermogravimetric analysis (TGA) of the fibers was performed using universal Netzsch 204 F1 (Phoenix, Ariz.). About 5 mg of the samples were heated at the rate of 10° C. $min^{-1}$ in an inert atmosphere with temperature ranging 0-500° C. using platinum crucibles. Differential thermal curves were obtained from the TGA curves by plotting a graph of derivative weight percentage as a function of temperature.

2.10 Differential Scanning Calorimetry

Differential scanning calorimetry (DSC) was performed to obtain thermal transitions and properties of materials using DSC Q2000 (TA Instruments, New Castle, Del.). The procedure started with a first heating ramp to reach 250° C., which was followed by a cooling step to 0° C., and then a second heating reaching 250° C. again. Heating and cooling rate was kept at 10° C. $min^{-1}$ under the nitrogen flow of 20 ml $min^{-1}$.

2.11 Assessment of Smooth Muscle Cell Attachment and Spreading

Rat pulmonary artery SMCs with passage of 6-10 were used for all the experiments. Cells were cultured in Dulbecco's Modified Eagle Medium (DMEM) (Corning, Corning, N.Y.) with 10% FBS (Atlanta Biologicals, Flowery Branch, Ga.), 2% L-glutamine, 1% non-essential amino acids and 1% Penicillin/Streptomycin at 37° C. with 5% $CO_2$ in T75 flasks. Upon confluency of SMCs, they were seeded on nitinol pieces coated with coaxially electrospun fibers as well as bare nitinol at a density of $3.3 \times 10^4$ $cells/cm^2$ in the complete culture media.

Cell attachment was evaluated based on the cell number on the stent material after 2 hr incubation. To perform the evaluation, samples were first washed with warm phosphate buffer solution (PBS) after aspiration of the media. Subsequently, samples were fixed with 4% paraformaldehyde (PFA; Sigma-Aldrich) in PBS for 20 min at room temperature, which was followed by washing twice in PBS for 5 min. The cells were then permeabilized with 0.5% Triton X-100 in PBS for 15 min. Subsequently, the cells were stained for F-actin with FITC-phalloidin (26.5 nM; Sigma-Aldrich) and 4', 6-diamidino-2-phenylindole (DAPI, 1 μg/mL; Sigma-Aldrich) diluted in 1.5% BSA in PBS for 30 min at room temperature). The samples were finally washed three times in PBS and mounted on microscope slides for examination using a fluorescent microscope. Cell count was analyzed with the "Analyze particles" tool in Image-J (National Institutes of Health). For quantification of cell numbers, the image was converted to 8 bit, and adjusted with a threshold.

2.12 Platelet Adhesion Assay

The blood compatibility of implantable materials was assessed by platelet adhesion study. The adhesion of platelet onto samples was studied by adding 300 μl of bovine platelet-rich plasma (Innovative Research, Novi, Mich.) to a 48-well tissue culture plate with samples on the bottom and incubating at 37° C. for 2 hr on a rotating table. After washing in PBS to remove unattached platelets, the samples were fixed using 2.5% glutaraldehyde at 4° C. for 2 hr, and then rinsed twice in PBS.

Some samples were then dehydrated through an ethanol series (30, 50, 75, 90, and 100%; 15 min each), and subsequently maintained in 100% ethyl alcohol until drying. They were dried overnight in a vacuum chamber and sputter-coated with gold before SEM (JEOL JSM6480 LV) to examine the number and morphology of platelets adhering to the surface.

2.13 Subcutaneous Implantation and Explant Evaluation

Prior to subcutaneous implantation, nitinol pieces coated with either coaxially-structured or layered fibers with 60 min crosslinking time, were soaked in 70% ethanol for ~15 min, followed by rinsing with sterile PBS three times, and then stored in prepared storage solution (1 mL dilute sterile PBS and 10 µl antibiotic solution of penicillin and streptomycin) for 24 hr. Rats were given Isoflurane anesthesia with at 5% per liter $O_2$ until fully anesthetized. Following anesthesia, an 8×5 cm square of mid dorsal skin was shaved, washed with ethanol, and then coated with betadine. Prepared samples were then placed on top of the subcutaneous musculature using a small incision. The incision was then closed using 9 mm autoclips (Kent Scientific, Torrington, Conn.). Finally, 50 µl of 1:1 ratio of Lidocaine and Bupivacaine mixture (Hospira, Lake Forest, Ill.) were injected between autoclips away from the subcutaneous pockets containing samples. After the implantation procedure, rats were monitored and moved to a clean cage over a heating pad set to 37° C. Their movements and signs of distress were closely monitored for the first 24 hr. The samples were retrieved after 7 days of the implantation.

For histological analysis, nitinol pieces, which were difficult to cut with normal histological setting, were first removed from the retrieved explants. The rest of explant tissues were then frozen with OCT as the freezing medium, following by quick freeze with dry ice. Two series of histological analysis were performed on the sample cross-sections cut with a cryostat: hematoxylin and eosin (H & E) staining (histology core, Anschutz Medical Campus, Aurora, Colo.) and immunohistochemistry staining with CD68 counterstained with hematoxylin. Immunohistochemistry on explanted frozen samples were first blocked with 10% wt albumin in TBS solution for 2 hr at room temperature in a humidity chamber. After removing the blocking solution, CD68 (6A324) primary antibody (1:100 in TBS containing 1% albumin) was added and left overnight at 4° C. in a humidity chamber. Then, slides were washed twice with 5 min each time in TBS-T under gentle agitation. Subsequently, binding protein mIgGk BP-B (sc-516142, Santa Cruz Biotechnology) with a dilution of 1:100 in TBS was applied and left for 30-45 min at room temperature in a humidity chamber, followed by washing three times in TBS, 5 min each time. Then, avidin D-HRP (sc516217) was applied for 30 min and rinsed 3 times for 5 min each time with TBS. ImmPACT NovaRED peroxidase substrate working solution was prepared following the manufacturer's manual, and applied for 2-15 min. Slides were then washed by running tap water over slides for 5 min and counter-stained with hematoxylin for nuclei by applying it for 1-5 min. Slides were washed with tap water until the rinse water was colorless. Then, slides were dipped 10 times in acid rinse solution (2% glacial acetic acid in DI water) followed by 10 dips in tap water. Finally, slides were dehydrated by soaking them sequentially in a series of solutions: 70% ethanol for 3 min, twice with 100% ethanol for 3 min each time, 1:1 of histoclear:100% ethanol for 3 min, and histo-clear for 3 min. For mounting, the mounting medium was added, a coverslip was placed on top and slides could dry for at least 1 hr prior to imaging.

2.14 Statistical Analysis

Statistical study was performed at least three substrates were used for each assay, and all assays were repeated in triplicate. All data are expressed as mean±standard deviation (SD). One-way analysis of variance (ANOVA) test was used to measure difference for experiments with multiple data sets with a Tukey multiple comparison tests performed between groups with significant difference. A p-value of ≤0.05 was considered statistically significant.

Figure 2:
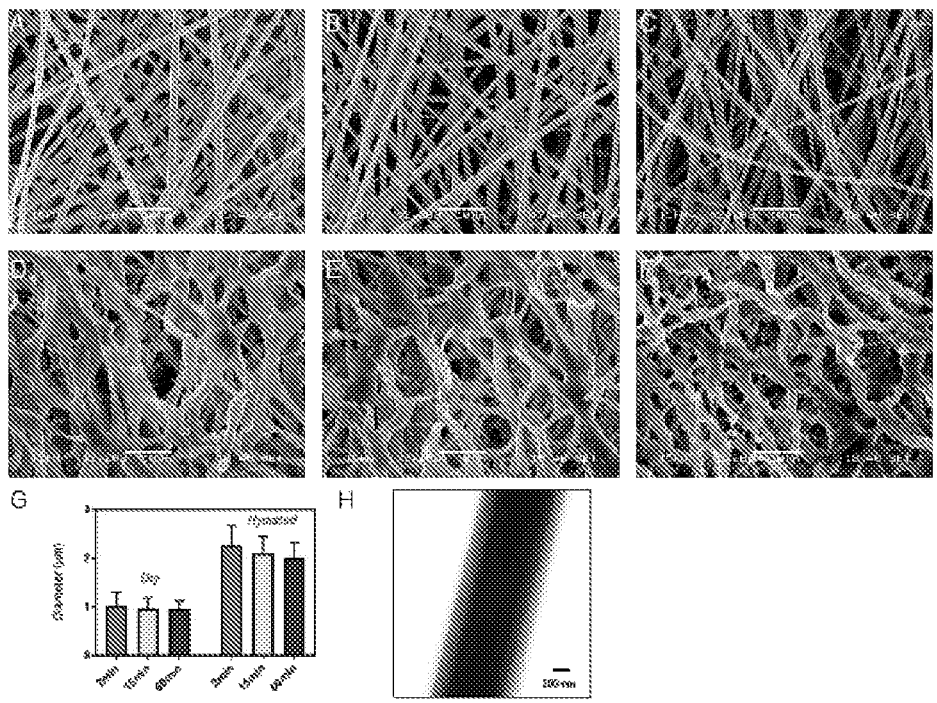
FIG. 2A-H shows micro-/nano-structure of coaxially electrospun fibers.

3 Results 3.1 SEM and TEM Imaging of Coaxially Electrospun PEGDMA/PLLA Coatings Showing their Micro- and Nano-Structure as Well as their Hydrogel Nature FIG. 2A-F shows the SEM images of the coaxially electrospun fibers made of PEGDMA-sheathed PLLA. Fibers are displayed in their dry state (FIG. 2A-FIG. 2C) and in their hydrated state (FIG. 2D-FIG. 2F). Images show that the 3D fiber networks have been formed and there are no apparent differences in the fiber morphology among samples polymerized with different UV exposure times. All the fibers exhibit obvious swelling after hydration, indicating the hydrogel nature of the PEGDMA sheath layer. Using Image-J software to analyze SEM images, fiber diameters were quantitatively determined (FIG. 2G). It was noted that the average diameter of coaxially electrospun fibers in hydrated samples with 2 min photopolymerization was slightly higher than those with 15 min or 60 min photopolymerization, likely due to the higher cross-linking degree under longer UV exposure time yielding less swollen fibers. In terms of material processing, the sheath solution is important to stabilize the core formation. Herein, the present invention has used PEGDMA in TFE with addition of PEO as the sheath solution. PEO was included as a carrier polymer to improve fiber formation during electrospinning. In order to obtain a stable fiber formation, varied concentrations of PEGDMA and PEO in the sheath solution were experimented. Smooth beadless coaxial PEGDMA/PLLA fibers with complete evaporation of solvent from the surface of the fibers were ultimately achieved, as demonstrated in FIG. 2A-FIG. 2C.

The nanostructure of the core-sheath coaxial electrospun fiber was visualized under TEM (FIG. 2H). The different structural density between the PLLA core and PEGDMA sheath resulted in distinct contrast in the TEM image. The inner darker region is corresponding to the PLLA core layer while the outside lighter region is to the PEGDMA sheath material. The core-to-fiber diameter ratio is 0.646±0.10, respectively. Previous work on electrospun coaxial fibers made of different types of materials also showed clear edges between core and sheath fibers [19].

To confirm the hydrophilicity of the coaxially electrospun PLLA/PEGDMA coatings, the coated surfaces were analyzed using water contact angle measurements. In all electrospun mats with varying UV photopolymerization times, the water drop, upon exposure to the surface, was immediately absorbed into the coated nitinol pieces, indicating their high hydrophilicity. Collectively, these results suggested the successful coaxial PEGDMA-sheathed PLLA fibers, having PEGDMA entirely covered the hydrophobic PLLA core and resulting in hydrophilic hydrogel coating on top of nitinol stent material.

Figure 12:
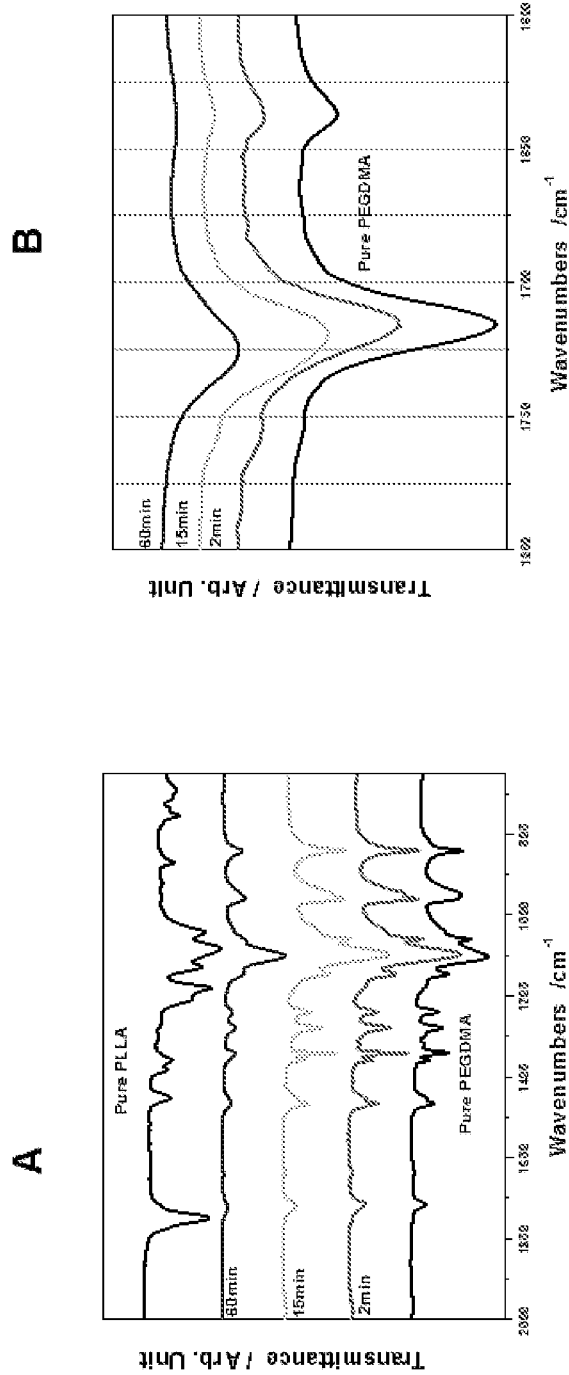
FIG. 12A&B shows typical FTIR spectra of the pure PLLA, PEGDMA, and coaxial PLLA/PEGDMA fibers in the entire scanned range (FIG. 12A), and in a specific range of 1600 to 1800 $cm^{-1}$ (FIG. 12B).

3.2 ATR-FTIR Spectroscopy Results Showing the PEGDMA Sheath of Coaxially Electrospun Fibers Varies with Photopolymerization Time To determine the effect of UV polymerization time on the chemical composition of the fibrous coating, FTIR analysis was carried out on coaxially electrospun PEGDMA/PLLA samples photopolymerized for 2, 15 and 60 min. Several functional groups of the products were examined. The infrared (IR) spectrum of coaxially-structured fibers, as shown in FIG. 12A&B, illustrated a series of characteristic bands of PEGDMA at 2800-3300 cm$^{-1}$ (O—H stretch), 1650-1739 cm$^{-1}$ (C=O stretch), 1635-1637 cm$^{-1}$ (C=C stretch), 1100-1150 cm$^{-1}$ (C—O acyl), and 960 cm$^{-1}$ (C—H bend). The fact that coaxially-structured fibers show all PEGDMA peaks, further confirm the coating of PEGDMA over PLLA fibers. Furthermore, it was found that the intensity of reactive acrylate peak (C=C) at 1635 cm$^{-1}$ decreased with the increase in the UV exposure time, and almost disappeared after 60 min indicating the nearly completed polymerization. Table 1 summarizes the calculated peak areas of C=O and C=C peaks, as well as the ratio of C=C to C=O peak. Since C=O stretch at 1650-1726 cm$^{-1}$ located in the close vicinity of C=C peak is a very strong peak independent of photopolymerization, the spectrum was normalized with C=O peak [20] The materials with 15 min and 60 min photopolymerization times showed 12% and 33% decrease, respectively, in the acrylate peak area, when compared with those polymerized for 2 min. The result agrees with our previous study utilizing PEGDMA alone with varied photopolymerization times [13]. Because a low concentration of reactive acrylates is present for the high molecular weight (3,000 Da) PEGDMA, the acrylate peak in the FTIR spectra displays low intensity. ATR-FTIR spectroscopy results demonstrated how the PEGDMA sheath of coaxial-structured fibers varies with the photopolymerization time in terms of its chemical composition.

TABLE 1

Analysis of FTIR data taken in absorbance mode from 400 cm$^{-1}$ to 4000 cm$^{-1}$ wavelengths for coaxially electrospun fibers with various photopolymerization times, showing the peak areas of C=O and C=C peaks, as well as the ratio of C=C to C=O peak.

| Photo-polymerization time [min] | Peak area: 1739-1675 cm$^{-1}$ | Peak area: 1650-1607 cm$^{-1}$ | Ratio [%] |
|---|---|---|---|
| 2 | 2.27 | 0.29 | 12.78 |
| 15 | 2.04 | 0.24 | 11.88 |
| 60 | 2.03 | 0.17 | 8.29 |

Since C=O stretch at 1650-1726 cm-1 located in the close vicinity of C=C peak is a very strong peak independent of photopolymerization, IR spectrum was normalized with C=O peak [20]. The peak area was determined with Origin Pro; data were taken in absorbance mode from 400 cm$^{-1}$ to 4,000 cm$^{-1}$ wavelengths. The samples with 15 min and 60 min photopolymerization times showed 12% and 33% decrease, respectively, in the acrylate peak area, when compared with those polymerized for 2 min. The analysis of ATR-FTIR curves shows that the majority of C=C bonds break to crosslink at two end methacrylate groups after 60 min of UV exposure due to the nearly completed polymerization reaction. The result agrees with a previous study utilizing PEGDMA alone with varied photopolymerization times [13]. Because a low concentration of reactive acrylates is present for the high molecular weight (3,000 Da) PEGDMA, the acrylate peak in the FTIR spectra displays low intensity.

3.3 Thermal Properties of Coaxially-Structured Fibers

Figure 14:
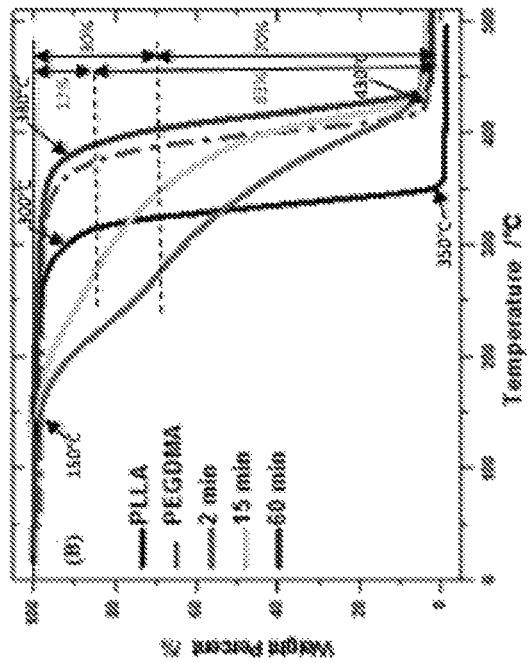
FIG. 14A&B shows thermoanalyses of PEGDMA, PLLA, and their coaxial fibers, as shown with (FIG. 14A) representative differential scanning calorimetry (DSC) curves during the second heating process, and (FIG. 14B) representative thermogravimetric analysis (TGA) curves.
Figure 14:
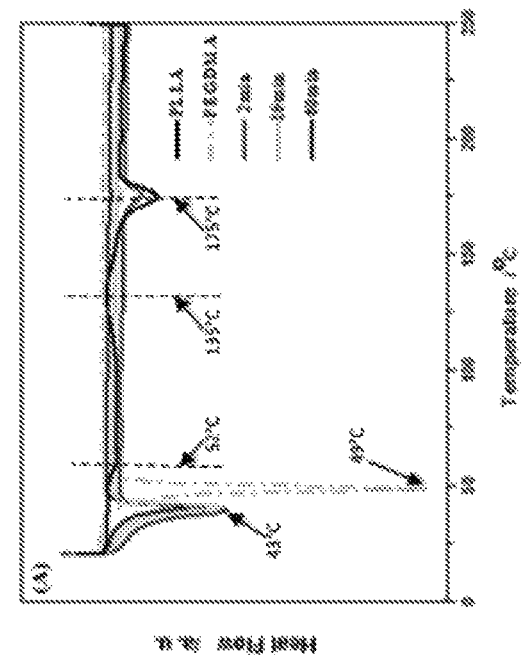

To further understand the material interactions in coaxially-structured fibers and the influence of UV polymerization on the fibrous materials, the thermal stability of the coaxially electrospun PEGDMA/PLLA coatings with varied polymerization times was evaluated using DSC and TGA. FIG. 14A and FIG. 14B show representative thermal behaviors of the coaxially electrospun mats as well as pure PLLA and PEGDMA mats. The pure polymers showed different transition temperatures when compared to coaxially-structured fibers. As shown in FIG. 14A, a sharp endothermic melting peak around 50° C. was found for pure PEGDMA [10], while the glass transition, crystallization, and melting peaks of PLLA were recorded at 52° C., 135° C., and 175° C., respectively. A slight shift to lower values for the PEGDMA melting temperature was found for all three types of coaxial fibers, as compared to that of the pure PEGDMA polymer. The decrease in the PEGDMA peak for PEGDMA/PLLA coaxial blends indicates the decreased crystallinity in the coaxial fibers as compared to pure PEGDMA. This might be due to the fast evaporation of the solvent during the electrospinning process, preventing the complete crystal formation. In the DSC thermogram of the coaxial blends, the only existing peaks are the ones representative respectively of PEGDMA and PLLA (though slightly shifted), which suggests the limited interaction between these two constituents. Interestingly, the intensity of PLLA melting peak is reduced with the increase of the UV exposure time, and nearly diminished for coaxial blends with 60 min UV exposure. This might be due to the fact that with increasing polymerization degree of PEGDMA sheathe (proportional to the UV exposure time), heat transfer from and towards the PLLA core could be obstructed. A more polymerized PEGDMA sheath serves as a better thermal insulator, so that the melting temperature of encapsulated PLLA likely increases to the region out of this specific DSC detection range. Hence, the interconnections between PEGDMA/PLLA fibers with longer UV exposure become stronger and denser. Because no additional peak formation was found, one may conclude that there is no chemical bond formation between core and sheath polymers so that the PLLA core and PEGDMA sheath are likely physically attached and/or mechanical interlocked.

To further elucidate the core-sheath interactions within the PEGDMA/PLLA coaxial electrospun systems with three different photopolymerization times, TGA was performed. The results in FIG. 14B showed a single-step weight loss for individual polymers of PEGDM and PLLA, while the coaxial blends with UV polymerization times of 2 min and 15 min underwent a two-step weight loss.

The initial weight percent loss of coaxial fibers with 2 min UV polymerization was ~30%, whereas those with 15 min polymerization was ~17% before reaching 300° C. More weight loss of coaxial fibers with shorter polymerization time may be due to the less crosslinked PEGDMA sheath, which can be less stable. Individual PLLA and PEGDMA polymers endured much higher thermal stability than the coaxial blends with short UV polymerization times (2 min and 15 min). PLLA was stable up to 300° C. showing a rapid weight loss at 300-350° C., whereas PEGDMA was stable up to 380° C. showing a rapid weight loss at 380-430° C. Nevertheless, all coaxial counterparts were found to be quite stable at least till 100° C. Therefore, all coaxial electrospun fibers exhibit sufficient thermal stability for their medical implant applications. The degradation profiles of coaxial electrospun fibers can be attributed to the combination of distinct materials in organized nanostructure. The two coaxial blends with 2 min and 5 min polymerization times exhibited the first step weight loss at a similar temperature (~150° C.), which might correspond to the decomposition of the PLLA core since they shared same properties. The drastic reduction in the weight loss temperature of PLLA within the coaxial system might be due to the pressure built up in the PLLA core, which lowered the degradation temperature. The onset temperatures of the second degradation step for the 2- and 15-min coaxial blends were close to that of PEGDMA, which can thus be assigned to PEGDMA decomposition. Interestingly, it was found that there was an increase in thermal stability of 60 min coaxial system with respect to that of 2 min and 15 min, possibly due to its high crosslinking density of PEGDMA. Highly crosslinked sheath might effectively prevent the PLLA degradation products from escaping the wrapped PEGDMA sheath, and thus no weight loss was detected. Therefore, the coaxial blend with 60 min UV polymerization follows the trend of the pure PEGDMA.

3.4 Mechanical Properties of Coaxially-Structured Fiber

Figure 13:
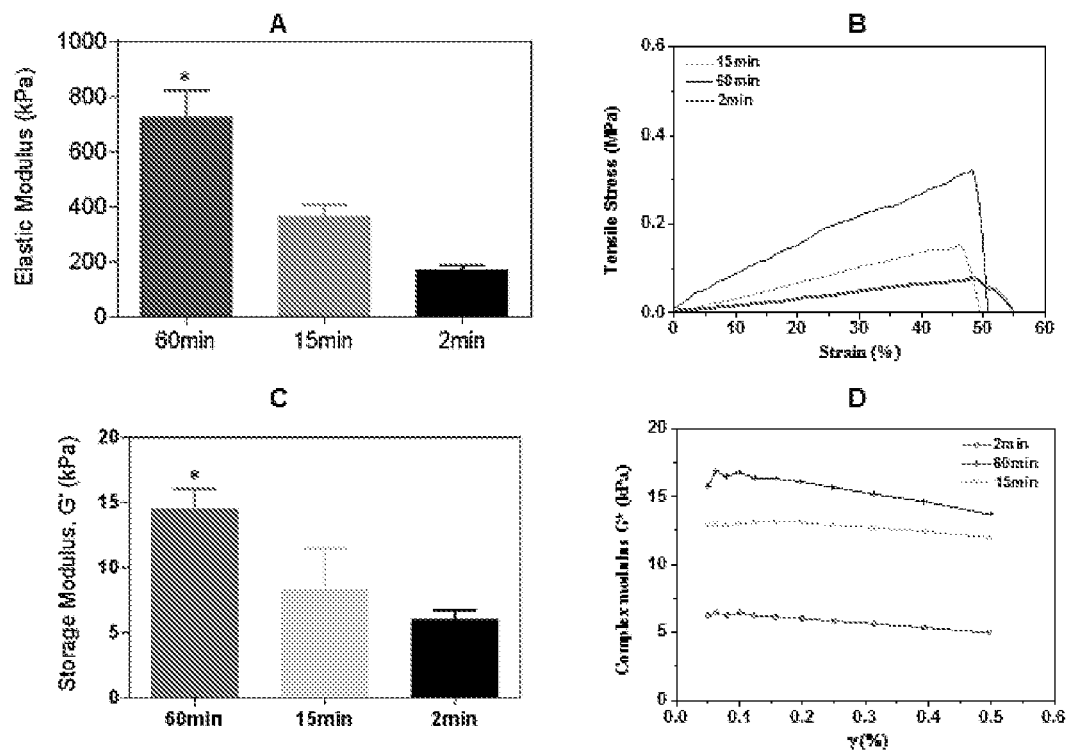
FIG. 13A-D shows mechanical characterization results of the coaxial PLLA/PEGDMA fibers.
Figure 15:
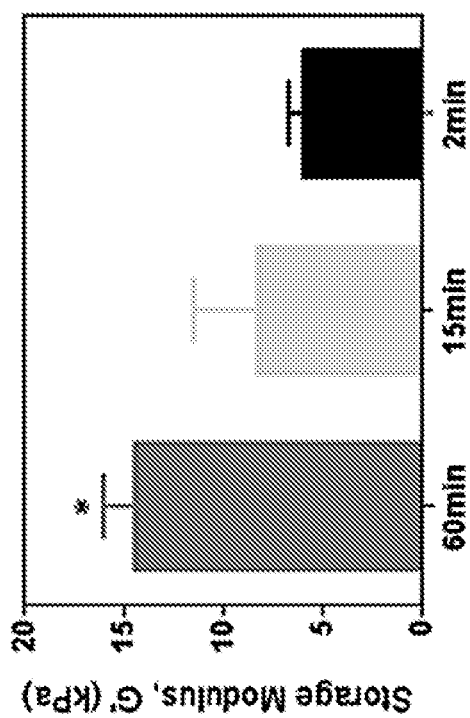
FIG. 15A&B shows a mechanical characterization results of the coaxial PLLA/PEGDMA fibers.
FIG. 15B shows storage modulus for samples with different UV photopolymerization times. "*" denotes significant difference of the denoted column from all the others with $p<0.05$.
Figure 15:
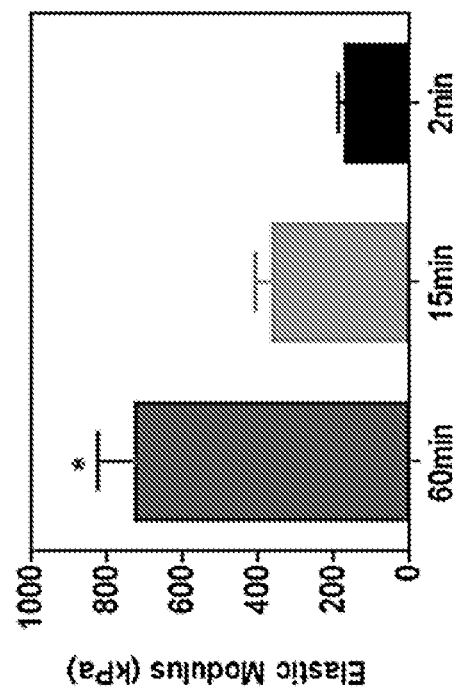

For vascular applications, materials strength and elasticity are both important. Thus, tensile testing and rheometry testing were performed to characterize mechanical properties of the coaxially-structured fibers. FIG. 15A shows the results from tensile tests on hydrated materials. The average elastic moduli of hydrated materials with 2, 15, and 60 min UV exposure times were 172, 366, and 729 kPa, respectively. The hydrated materials with 60 min photopolymerization time exhibited highest elastic modulus and strength. FIG. 13B illustrates representative stress-strain curves of these materials. Stress and strain at break as well as the Young's modulus of these fibrous coatings were shown in Table 2. Rheometry was further used to show dynamic viscoelastic properties of these materials. FIG. 15B demonstrates the storage modulus for each sample and FIG. 13D shows curves of the complex modulus, G*. Storage moduli vary from 6.5 kPa for 2 min samples to 14.5 kPa for 60 min samples, with the modulus increasing with the photopolymerization time. The results are in good agreement with our previous findings that reported the photopolymerization times of PEGDMA produced scaffolds with varying stiffness [13, 21]. The storage modulus values of coaxially-structured fibers are around 3 folds of those PEGDMA fibers for each polymerization time. Rheometry tests in strain sweep showed the linear viscoelastic regions located in the similar strain ranges for all three samples with varied photopolymerization time, indicating similar dynamic mechanical responses for all samples. It is likely that the increase in the UV exposure time of PEGDMA led to increased crosslinking density of PEGDMA and interfibrillar connection as well as physical entanglement of the polymer chains, leading to higher elastic modulus of coaxially-structured fibers with a constant PLLA core. Also, the rheometry results agreed with tensile testing results, showing the highest modulus for materials with 60 min polymerization and lowest for those with 2 min polymerization. However, the elastic modulus values from mechanical tests are more than 10 times of the storage moduli (G') yielded from rheometry test. Overall, the results on the mechanical property characterizations of coaxial fibers are listed in the Table 2. Thus, the mechanical strength of coaxially-structured fiber scaffolds improved with increased photopolymerization time.

FIG. 13A shows the results from tensile tests on hydrated samples. The average elastic moduli of hydrated samples with 2, 15, and 60 min UV exposure times are 172, 366, and 729 kPa, respectively. Among the three types of PEGDMA samples with varied polymerization times (i.e. 2, 15, and 60 min), the hydrated sample with a photopolymerization time of 60 min shows the highest value in elastic modulus. Stress and strain values as well as the Young's modulus of the fibrous coatings were determined from load-displacement curves. FIG. 13B illustrates the representative stress-strain curves of samples.

FIG. 13C demonstrates the storage modulus for each sample and FIG. 13D shows changes of the average complex modulus, G*. Storage moduli vary from 6.5 kPa for 2 min samples to 14.5 kPa for 60 min samples, with the modulus increasing with the photopolymerization time.

The results are in good agreement with previous findings that reported the photopolymerziation times of PEGDMA produced scaffolds with varying stiffness [13]. The storage modulus values of coaxially-structured fibers are around 3 folds of those PEGDMA fibers for each polymerization time. Rheometry tests in strain sweep showed the linear viscoelastic regions located in the similar strain ranges for all three samples with varied photopolymerization time, indicating similar dynamic mechanical responses for all samples. It is likely that the increase in the UV exposure time of PEGDMA leads to an increase in the crosslinking density of PEGDMA and interfibrillar connection as well as physical entanglement of the polymer chains, leading to an increase in elastic modulus of materials with constant PLLA core material. By performing rheometry tests, dynamic viscoelastic properties including the storage modulus, G', the average complex modulus, G*, and shear stress values under the constant strain were determined. The rheometry results were in agreement with the tensile testing results, showing the highest values for 60 min UV polymerized samples and the lowest values for 2 min UV polymerized ones, though the modulus values from mechanical tests are more than 10 times of those yielded from rheometry test. Overall, the results on the mechanical property characterizations of coaxially electrospun fibers including average tensile modulus and dynamic modulus (G' and G") are listed in the Table 2.

TABLE 2

Mechanical properties of coaxially-structured scaffolds

| | Photopolymerization time [min] | | |
|---|---|---|---|
| | 2 | 15 | 60 |
| Average elastic modulus, E (kPa) | 172 ± 15 | 366 ± | 729 ± |
| Average storage modulus, G' | 6.0 ± 0.71 | 8.4 ± | 14.5 ± |
| Average loss modulus, G" (kPa) | 0.36 ± | 0.78 ± | 1.4 ± |
| Average stress at break, σb (kPa) | 82 ± 7 | 157 ± | 325 ± |
| Average strain at break, Eb (%) | 48.3 ± 5 | 43.6 ± 4 | 48.4 ± 5 |

3.5 Attachment of Vascular SMCs and Platelets

The attachment of SMCs and platelets were studies in order to evaluate the potential of the coaxially-structured fiber coatings for vascular stent implants. The SMCs were cultured on the nitinol pieces coated with coaxially electrospun fibers as well as on the bare nitinol piece. After 24 hours of culture, the cells were stained with DAPI for cell nuclei and F-actin, and representative fluorescent images were shown in FIG. 16A-D. The bare nitinol showed considerable cell attachment and spreading. By contrast, all nitinol pieces coated with coaxial PEGDMA/PLLA fiber matrices displayed much lower cell attachment and the attached cells were less spreaded. The quantification of the cell area coverage shown in FIG. 16E confirmed the strong inhibitory effects of the PEGDMA/PLLA matrices on the attachment and spreading of SMCs when compared to the bare nitinol. It was also interesting to note that the coaxial PEGDMA/PLLA fiber matrix with 60 min UV exposure showed slightly higher cell coverage than 15 min and 2 min ones, which might be due to the matrix stiffness effects on promoting cell attachment and spreading.

Platelet attachment results, as shown under SEM imaging (FIG. 17A-D), demonstrate that more platelets are attached to bare nitinol when compared to nitinol pieces coated with coaxial fibers after 60 min, 15 min or 2 min UV polymerization. In addition, the shape change of platelets is an indicative of platelet activation, and according to Ko et al. [22], can be classified into five stages in the following order: discoid or round, dendritic, spread-dendritic, spreading, and fully spreading. In the present invention, it was found that platelets were more aggregated, accumulated together and fully spreaded on the bare nitinol, indicating that a high degree of platelet activation on the bare nitinol. By contrast, smaller-sized, less-spreaded platelets on nitinol pieces with PEGDMA/PLLA coatings with 2, 15 and 60 min UV polymerization times were found. Platelets on these polymeric coatings remained spherical and separated. The low attachment and low activation level of platelets demonstrate the role of the photopolymerizable PEGDMA in truncating the adverse reactivity of stent material surface with blood component platelet.

3.6 Coaxially-Structured Fibers for Stent Coating

To demonstrate the feasibility of coaxially-structured PEGDMA/PLLA fibers as a potential coating material on vascular stents for future implantation studies, a small-diameter vascular stent was used for the development of coating protocol. As shown in FIG. 20, the present invention presents a successfully developed a new coating process, yielding a thin coating of coaxially-structured fibers uniformly deposited on both the interior lumen and abluminal surface of a vascular stent. In one embodiment of the present invention relates to a protocol quite different from the few approaches used in the development of biological tissue covered stents [23]. The complete coverage of bioinert, mechanically stable hybrid fiber coating on metallic stents in a sandwich like configuration provides a novel method to control biological responses, which may be further designed for drug-eluting function.

3.7 Evaluation of Coaxially-Structured Fibrous Materials with In Vivo Grafting To demonstrate the effectiveness of coaxially-structured PEGDMA/PLLA fibers as a potential vascular implant material, when compared to a layered configuration of PLLA and PEGDMA fiber materials, bare nitinol pieces were coated with nanostructured fibers or layered of PEG polymer and implanted into rats. Because SMC attachment and platelet adhesion assays suggested little biological differences among coaxiallystructured PEGDMA/PLLA fiber materials with varied polymerization times, the in vivo studies were only performed on samples with 60 min polymerization time, which was compared with layered fiber materials polymerized for the same time.

FIG. 18A demonstrates in vivo tissue response to the implants. The explant images show that polymercoated nitinol pieces exhibited tissue encapsulations at varied degrees upon retrieval, while bare nitinol piece was surrounded by blood capsule or pocket (FIG. 19), which was consistent with the platelet adhesion results. The blood pocket was fragile, so that its structure was difficult to maintain for cutting and subsequent histological analysis. Histological and immunohistochemical analyses demonstrated comparisons between coaxially-structured and layered PEGDMA/PLLA fiber materials. Quantitative analyses of histological images in FIG. 18B reveal that the encapsulation layer thickness was significantly thinner around coaxially-structured materials, when compared to layered materials. Representative histological images further demonstrated that the tissue encapsulation around the layered materials when compared to coaxial materials were more cellular, suggesting more cell infiltration during acute inflammation stage (i.e. Day 1 to Day 3), in particular on the outer side of encapsulation. Tissue encapsulation around coaxially-structured materials, on the other hand, presented uniform, consistent structure with a thin layer of more striated cells, indicating healing and end of inflammation. In addition, the layer separation was obvious in the layered fiber materials. The delamination might be due to the limited interface between two constituting polymer chains with distinct physico-chemical properties (i.e. hydrophobic PLLA and hydrophilic PEGDMA), which likely elicited a higher amount of inflammation in response to both PLLA and PEGDMA layers or to the irritation from the movement of the layers therefore. Notably, the coaxial fiber structure provided large interfacing areas for these polymer chains, which allow for stronger, nano-scale interplays between two constituents leading to more stable structure and complete encasement of PLLA within bioinert PEGDMA. As chronic inflammatory responses often involve macrophages, immunohistochemistry staining was further used to detect CD68-positive or M1 macrophage cells. All images revealed there were very few CD68-positive cells in both inner (facing the implant) or outer (facing the surrounding tissue) sides of the encapsulation tissues in these two types of fiber coatings. This suggested both coatings had an overall low level of chronic inflammation and good biocompatibility. Yet, few CD68-positive cells were noticeable in the inner side of the layered but not coaxial fiber materials. Therefore, coaxially-structured fiber materials might be more favorable with reduced cell inflammation and tissue encapsulation.

4 Discussion

The present invention describes the development of new coating materials made of nano/micro-sized coaxially hybrid fibers which may be used to improve the performance of vascular implants. A hydrophilic sheath PEGDMA was used to coaxially cover a hydrophobic PLLA core, in favor of creating an excellent combination of mechanical stability, tunable elasticity and bioinert surface. The coaxial microfibers, as coating over stent metals, strongly reduced SMC overgrowth and discourage platelet adhesion and activation, compared to bare metals. Such coatings exhibited soft gel-like, high-water-content surface like PEGDMA but much higher strength with properties resembling vascular tissues. To examine the effect of surface mechanics, the results showed that the surface stiffness did not significantly change the structure such as 3D network, fiber diameter and fiber density. However, the small differences in the elasticity of coaxially-spun coatings polymerized with varied times influences the attachment of platelets and arterial SMCs on the coated metallic pieces Regarding the coaxial fiber stiffness, a previous study correlated tensile modulus of coaxial fibers with their core diameter rather than their core material [24]. As the diameter and material of the core for the samples UV polymerized for 2, 15 or 60 min are similar, the difference in the mechanical testing results presented here is attributed largely to the mechanical differences in the sheath characteristic of coaxial PEGDMA/PLLA systems. The rheometry and tensile testing results both showed that the mechanical modulus and strength were the highest for 60 min UV polymerized samples and lowest for 2 min UV polymerized ones. Therefore, the gel-like fibrous coating is softer when less cross-linking of PEGDMA occurs with shorter UV exposure time. Different photopolymerization times may also affect the interface diffusion between the core and sheath as well as the interaction between PEGDMA and PLLA during coaxial electrospinning, which further contributes to distinct elasticity of the matrix. Interestingly, the tensile modulus and storage modulus obtained from the present invention 3D fibrous coaxially-structured materials did not follow the equation that is often used to relate the two moduli for a variety of materials:

$$E' = 2G'(1+v),$$

where E represents elastic modulus, G' represents storage modulus, and v is the poisson's ratio with a value between 0 and 1, e.g. v=0.5. This equation was often used to correlate modulus obtained from different measurements in the application of solid polymers or composite materials. The fact that our 3D hydrogel did not show similar correlation might be due to the hierarchical material interfaces, engaging different response mechanisms under tensile and shear stresses. They do not show similar correlation, which might be due to the hierarchical interfaces of the materials, offering novel mechanical behaviors. Such mechanical behaviors simulating vascular tissue characteristics, might be important to tissue engineering applications, where both macroscale mechanical strength and microscale softness are needed to ensure the overall structural strength to withstand mechanical forces as well as the local hydrated and elastic environments for proper cell functions.

Our fiber system is characterized by artery-like elasticity and multiscale mechanics, simulating collagen rich arterial matrices in adventitial and medial layers. Single collagen matrix fibrils exhibit extremely high tensile modulus [25, 26], while provide soft microenvironments for arterial cell functionality [13, 21], and macroscopic measures of tissue [27, 28]. Such biomimetic fiber system might be important to tissue engineering applications, where both macroscale strength and microscale softness are required to ensure the overall structural strength to withstand mechanical forces and the hydrated, soft microenvironments for cell function.

Although not limiting the present invention to any particular application, it is believed that one major application field for the present invention developed PEGDMA/PLLA fibers lies in the coating of vascular stents. To demonstrate the feasibility of coaxially-structured PEGDMA/PLLA fibers as a potential stent coating, a small diameter stent was used to demonstrate protocols. FIG. 20 illustrated this new coating process. Thin coatings of coaxially-structured fibers were uniformly deposited on both interior lumen and abluminal surface of the stent. Results demonstrated highly conformal coating, flexible and elastic to fit stent geometry. The protocol presented herein was different from previous stent coating approaches [23]. The complete coverage of metallic stents with bioinert, mechanically robust hybrid fibers may provide a novel method to control biological responses. Due to existing limitations in the deployment of bare metal stent and drug-eluting stent, the next generation of stents could be those with multi-functional coating designed to create favorable stenting micro-environments that cater to desired short-term and long-term biological responses from neighboring vessels [23]. The selection of PLLA and PEGDMA for potential stent coating materials was based on their unique properties and their wide uses in the biomedical field. PLLA has gained significant attention due to its excellent biocompatibility and biodegradability, its use for drug eluting, as well as commercial availability. PEGDMA has unique properties such as lack of toxicity and excellent antifouling capability that prevents protein adhesion, and it can be easily eliminated from body. One benefit of composite coating scaffold using a combination of diverse polymeric materials lies in the possibility of synergizing the favorable characteristics of each individual component to obtain superior mechanical and/or biological properties required for specific medical challenges such as vascular stenting. Using micro-/nano-fibers with different physical properties such as hydrophobic/hydrophilic properties and degradation rates, one embodiment of the present invention has combined PEGDMA and PLLA into a coaxial structure to form hybrid fibers, providing unprecedented characteristics. The hydrophilic/hydrophobic characteristic is a critical factor that affects protein adhesion and thus influences blot clot formation and cell adhesion. It also affects biomolecule release and mechanical properties. The hydrophobic nature of polymers such as PCL, PU and PLA tend to attract platelet and plasma protein adhesion, which results in the platelet aggregation and intimal hyperplasia of the artificial blood vessels [18]. To that end, the material design uses the hydrophobic, degradable core to provide the mechanical stability of the scaffold, while the sheath enhances biocompatibility. The composite nanofiber made of hydrophobic PLLA and hydrophilic PEGDMA synergizes the advantages of two polymers and gives rise to better thrombotic resistance that hydrophilic polymers can offer together with superior mechanical properties and higher molecule incorporation potential that hydrophobic polymers may provide. It may also improve hydrolytic resistance when compared to pure PLLA. With the hydrogel characteristic, the present invention PEGDMA/PLLA coaxial system may also be immediately integratable with biological systems.

Besides the advantages offered by the fiber surfaces, the PLLA core of the fibrous coating may offer therapeutic advantages, serving as a reservoir of bioactive molecules such as anti-proliferative drugs, regenerative proteins or anti-thrombotic molecules. To illustrate such potentials, we have characterized the release profile of heparin utilizing heparin-impregnated PLLA (FIG. 21). This approach can further address long-term issues, with most prominent ones being stent-induced vascular wall injury, which lead to SMC overgrowth (i.e. restenosis) and/or thrombosis[29]. In addition to drugs, multi-functional coating can also be designed to create pro-regenerative microenvironments [23].

Overall speaking, coaxial micro-/nano-fibers made from polymeric materials with diversely different physico-chemical properties (e.g. PEGDMA and PLLA), with properly designed hierarchical structure, can demonstrate unprecedented characteristics advantageous for vascular implants. Efforts should be taken to design the nanostructure and define the fabrication process for such hybrid fibers, in order to synergize individual components for superior stent or graft performances, e.g. regenerative surfaces, controlled drug or molecule release, mechanics, and degradation profile. Two limitations of this study are acknowledged here. The first is related to the chemical degradation of fibers over time. In lieu of that, we have shown the chemical decomposition kinetics and stability using TGA instrument, which can be used to predict chemical degradation characteristics. The second is the evaluation of vascular stents in vivo, which requires a new animal protocol for deploying such coated stents.

Stenting procedures has advanced the field of interventional cardiology, but problems, with most prominent ones being stent-induced vascular stenosis and thrombosis, often occur in clinic. During the stent placement, the vascular wall undergoes significant expansion leading to the de-endothelialization of the tunica intima and in turn SMC growth in the lumen, which often causes thrombosis, reoccurrence of lumen narrowing and dissection of the vessel wall [29]. Fragmentation of endothelial layer due to stenting often results in restenosis or the overgrowth of SMCs. Stenting-induced injury within the arterial wall can cause SMC injury, followed by SMC proliferation, migration, and extracellular matrix deposition. Therefore, methods to alleviate the contributing factors towards in-stent thrombosis and in-stent restenosis would be of great clinical importance. To inhibit protein and platelet from attaching to the material surface, PEG-based materials are frequently utilized by previous researchers [30]. An effective interplay and a synergistic cooperation between cells and stent surfaces have been proven to be a critical factor for the process of stent-tissue integration and, eventually, for vascular tissue regeneration over or around the stent. Specifically, synthetic polymers are attractive because they can be fabricated into various shapes with desired morphologies and features which can be permissive for cell maintenance and ingrowth. In addition, these polymers can be fabricated reproducibly with specific molecular weights, block structures, degradable moieties, and cross-linking mechanism. These properties in turn, govern material formation dynamics, cross-linking density, and material mechanical and degradation properties. The present invention contemplates embodiments that may incorporate anti-proliferation drugs and specific signaling molecules such as peptides into the existing co-axial systems. Specifically, in one embodiment the hydrophobic, degradable core could provide controlled drug release and the sheath may further be designed to integrate surface signaling mechanism that simultaneously aid in regeneration. Although not limiting the present invention to an particular embodiment, it is believed that this may also extend to in vivo studies which use the present invention developed protocol to coat stents and evaluate coated implants on experimental animals.

5 Conclusion

Taken together, the fabricated coaxially electrospun coatings on the stent are mechanically stable and have highly-hydrophilic, non-adhesive, non-interacting and inert surface, hindering the attachment of SMCs and platelets, suggesting the potential of the coaxial PEGDMA/PLLA fibers as a coating for vascular stents. Truncation of SMC overgrowth and platelet adhesion on a biomaterial surface is a competent advent to hamper restenosis and thrombosis incidents after stent implantation.

Presented herein is a novel nanostructured fiber scaffold composed of coaxially-interfaced PLLA and PEGDMA. The photo-crosslinkable nature of the composite fiber, together with the excellent integration of PLLA within the PEGDMA sheath, allowed the creation of a hydrogel construct with mechanical strength to withstand forces in vivo and non-adhesive surface. The bioinert surfaces hindered attachment of SMCs and platelets and reduced inflammation and tissue encapsulation in vivo. The photo-crosslinking density can further fine-tune the surface properties of coaxially-structured fibers. An optimal UV polymerization time might be 15 min, as it demonstrated the moderate elastic and storage modulus as well as acceptable platelet attachment area ratios along with low SMC attachment area ratios. These results provide evidence to support the potential use of the nanostructured fiber scaffold for vascular implants, offering mimicry of both structural and biological characteristics of native arterial tissues.

Figure 1:
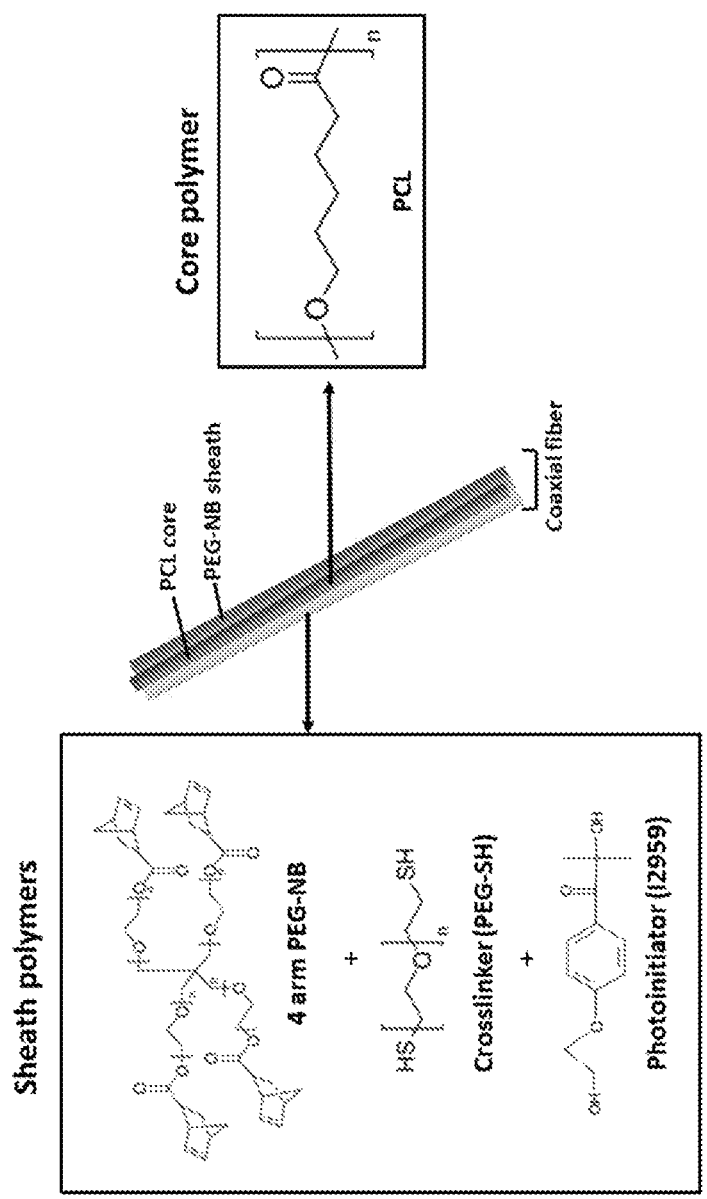
FIG. 1 shows one embodiment of the invention composition of the polymers used to make the hydrogel scaffolds, with fibers made with a PCL core and a PEG-NB-PEG-SH sheath.

6 Coaxial PCL/PEG-Thiol-Ene Microfiber with Tunable Physico-Chemical Properties for Regenerative Scaffolds Fabrication of Coaxial Fibers The apparatus used for obtaining coaxial fibers was developed in-house. The core hydrophobic polymer solution was passed through the inner needle of 22 G (0.71 mm in internal diameter), while the sheath hydrophilic polymer solution was passed through the outer needle of 18 G. A dual syringe holder was used to place the syringes loaded with polymer solutions. This design allows the solutions to be extruded simultaneously. Polymer solutions of 1.8 wt % concentration of PCL and 3 wt % 4-arm PEG-NB 5 kDa (synthesized in-house) or 4-arm PEG-NB 10 kDa were prepared by dissolving a predetermined amount of PCL, PEG-NB 5 kDa or PEG-NB 10 kDa, PEG-SH (JenKem Technology, Dallas, Tex.), PEO, and Irgacure 2959 (Ciba Speciality Chemicals, Basel, Switzerland) in 1,1,1,3,3,3 hexafluoro-2-propanaol (HFP, CovaChem, Loves Park, Ill.). FIG. 1 shows the composition of the different polymers used for the hydrogel's fibers. The solutions obtained after stirring for 30 $min^{-3}$ h were loaded in 5 mL syringes connected to the positive terminal of a high voltage ES30P 10 W power supply (Gamma High Voltage Research, Ormond Beach, Fla.). The core polymer solution was extruded at 0.8 mL $h^{-1}$ and the sheath polymer solution at 1 mL $h^{-1}$ using syringe pumps (Pump 11 Plus, Harvard Apparatus, Boston, Mass.) and subjected to an electric potential of 11 kV. The fibers were deposited onto a grounded static aluminum substrate placed at a distance of 15 cm perpendicular to the needle. The obtained samples were stored at room temperature until further use.

Crosslinking of Fibrous Scaffolds with UV Polymerization

The scaffolds composed of coaxial fibers were subjected to vacuum for 15 min for oxygen removal using a glovebox (Vacuum Atmospheres Company, OMNI-LAB, Hawthorne, Calif.) containing argon. After that, the scaffolds were cross-linked by UV light (supplied power ~5 mV $cm^2$) for varied UV times. Immediately after the crosslinking process, fibrous scaffolds were rinsed with phosphate buffered saline (PBS, pH 7.4) and used for mechanical characterization (tensile and rheometry testing), or subsequently lyophilized for 48 h to obtain dry samples for ATR-FTIR spectroscopy, thermal analyses, and SEM. For cell and animal studies, the samples were treated with RGD 5 mM after PBS rinse. The clickable thiol-ene PEG photo-polymerization occurs through a reaction between the "ene" groups present in the 4-arm PEG-NB norbornene rings and the thiol groups of the poly(ethylene glycol) dithiol (PEG-SH), which is used as the cross-linker. A step-growth mechanism leads to a highly homogenous distribution in cross-links, thus imparting tunable substrate stiffness through UV exposure time. For most characterization and biological studies, two UV doses were used by changing the UV exposure time: 10 min UV polymerization for low UV dose, and 60 min for high UV dose.

Thermal analysis-thermogravimetric analysis and differential scanning calorimetry analysis. Thermogravimetric analysis (TGA) of the fibers was performed using a Mettler TG50 thermobalance under flushing nitrogen (100 mL min$^{-1}$). About 10 mg of the samples were placed in a nitrogen atmosphere and heated at 10° C. min$^{-1}$ starting at the room temperature and up to 700° C. Both cross-linked fibers and fiber meshes were analyzed. The decomposition temperature ($T_d$) corresponding to the temperature associated with the maximum mass loss rate was determined. Pure polymers, including PEG-NB 5 k, PEG NB 10 k, PEO (Mn=400 000), and PCL (Mn=80 000, in pellet and fiber forms), were used as reference materials Differential scanning calorimeter (DSC Q20, TA Instruments, USA) was performed under flushing nitrogen (100 mL min$^{-1}$). Specifically, about 10 mg of the samples was placed in a heating chamber, and constant nitrogen gas flow and heating-cooling-heating cycles were performed. Each sample was first heated from 5° C. to 100° C. with an incremental rate of 10° C. min$^{-1}$ to eliminate the thermal history of the materials. The samples were then fast cooled to 5° C. at a cooling rate of 25° C. min-1 and reheated for a second scan up to 100° C. at a rate of 10° C. min$^{-1}$. The same reference materials used in TGA were included in DSC measures. The melting behavior of PEG-NB species after crosslinking was determined by monitoring the endothermic melting peaks. The respective proportion in the coaxial PCL/PEG-NB samples was determined from the intensity of PCL melting peak in the second scan. Specifically, the enthalpy of fusion related to PCL melting for pure PCL samples and PCL/PEG-NB coaxial samples were quantitatively determined by calculating the area of the endothermic melting peak. The crystallinity degree of PCL ($\alpha$PCL) was determined by comparing the enthalpy of fusion of pure PCL fibers ($\Delta$HPCL) with the theoretical value of a 100% crystalline PCL ($\Delta$H100%), which equals to 139.4 J g$^{-1}$ [31]. Thus, $\Delta$PCL=100×($\Delta$HPCL/$\Delta$H100%). Under the assumption that crystallinity degree of PCL ($\alpha$PCL) remained constant in the case of coaxial fibers, $\alpha$PCL was used to determine the fraction of PCL in the coaxial samples.

Cell Attachment and Compatibility of Coaxial Fibers

Bovine pulmonary artery endothelial cells (bPAECs) from Lonza Inc. (Basel, Switzerland) were seeded on top of coaxial fiber scaffolds with a seeding density of 5×10$^4$ cells per cm$^2$ at 37° C. and 5% CO$^2$ for 24 h. Cells at passage 9 were used. Treated glass slides were also used for cell attachment studies. Before cell seeding, the coaxial fiber scaffolds were treated with 5 mM CRGDS (GenScript Inc., Piscataway, N.J.), which was covalently bonded to the PEG-NB through UV light (5 min of UV exposure). Then, the scaffold samples were rinsed with PBS to remove unattached RGD, sterilized with 70% ethanol for 15 min, and rinsed again three times with sterile PBS. The cell culture medium was composed of MEM Eagle D-Valine medium modified with 4 mM L-glutamine (US Biological Life Sciences, Marblehead, Mass.), 20% FBS (Corning, 35-0101-CV), 50 µg mL$^{-1}$ gentamicin, and 70 µg mL−1 heparin. To evaluate cell attachment and morphology, the cell-seeded scaffolds were rinsed with PBS after 24 h of cell seeding, fixed using 4% formaldehyde, and stained with DAPI and F-actin. The stained cells were examined with appropriate filters using a fluorescent microscope at 10× and 40× magnification. The number of cells attached to each scaffold was determined using ImageJ software.

Materials Implantation and Explant Evaluation

Five groups of scaffold samples (n=5-7 for each group) were evaluated: PCL/PEG-NB 5 kDa and PCL/PEG-NB 10 kDa coaxial fiber scaffolds polymerized with low or high UV dose, and PCL fiber scaffold. The prepared fibrous materials were cut into circular disks (1 cm diameter). Prior to implantation, materials were treated as those for in vitro cell culture. The sample evaluation was performed on Sprague Dawley rats at 8-9 months old at the time of the implantation, weighing ~400 grams. The rats were purchased from ENVIGO (Indianapolis, Ind.). Anesthesia in rats was induced with 5% isoflurane gas (Vet One) and maintained with 2% isoflurane gas. Surgical site was cleaned and disinfected with povidone-odine (Medline Industries Inc, Northfield, Ill.). Rats were given isoflurane anesthesia at 5% per liter O$_2$ until fully anesthetized. Following anesthesia, mid ventral skin was shaved, washed with ethanol, and then coated with betadine. Rats were transferred to a procedural table that was cleaned with 70% ethanol solution and covered with a clean disposable towel. A sterile disposable blade was used to make the incision and create a 1.5 cm×2 cm subcutaneous pocket. Material samples were then placed on top of the subcutaneous musculature. The incision was then closed using 9 mm autoclips (Kent Scientific, Torrington, Conn.). Finally, 50 µL of 1:1 ratio of lidocaine and bupivacaine mixture (Hospira, Lake Forest, Ill.) were injected between autoclips away from the subcutaneous pockets containing samples. After the implantation procedure, rats were moved to a clean cage over a heating pad set to 37° C. Their movements and signs of distress were closely monitored for the first 24 h. The samples were retrieved after 7 days of the implantation.

The explanted samples were embedded with OCT and cryosectioned into 8-10 µm thick sections. The sections were stained with hematoxylin and eosin (H&E) and Masson's Trichrome, which were performed by the Histology Core at University of Colorado. Imaging was performed with a light microscope (Nikon Microscopy). To determine materials induced inflammation, immunofluorescent staining with CD68 to detect the macrophage presence was used with DAPI counterstain. Briefly, the explanted frozen samples were blocked with 10% wt albumin, then applied with CD68 (6A324, Santa Cruz Biotechnology, Dallas, Tex.) primary antibody (1:100 in TBS containing 1% albumin), and finally applied with secondary antibody mIgG (Santa Cruz Biotechnology, Dallas, Tex.) with a dilution of 1:100 in TBS.

Dual-Modality Multiphoton Imaging

To determine the matrix production in scaffold implants in rats, dual modal multiphoton imaging, including second harmonic generation (SGH) and two-photon excitation fluorescence (TPEF), was used to respectively investigate the fibrillar collagen and elastin contents. The sectioned samples were mounted on glass slides, submerged in PBS, and covered with a coverslip. For SGH and TPEF imaging, a multiphoton laser scanning microscope system (Radiance 2000 MP, Bio-Rad Laboratories Inc, Hercules, Calif.) was used with 40× magnification (n.a.=1.30), oil immersion objective. A femtosecond pulsed laser system tuned to 860 nm wavelength was used for excitation (Spectra-Physics, MaiTai wideband, mode-locked Ti: Sapphire laser system). The response signal was split at 455 nm using a dichroic mirror (AT455 DC, Chroma Technology Corp, Bellows Falls, Vt.). The SHG signal (400-455 nm) for collagen and the TPEF signal (460-610 nm) for elastin were captured simultaneously using the direct detector system. A 535/150 nm BrightLine bandpass filter was used for elastin TPEF capture. Images 1024×1024 pixels (305×305 microns) were collected at 50 lps. Each image was generated using Kalman averaging over 3 frames.

Morphology of the Hybrid Coaxial Fibers

Figure 3:
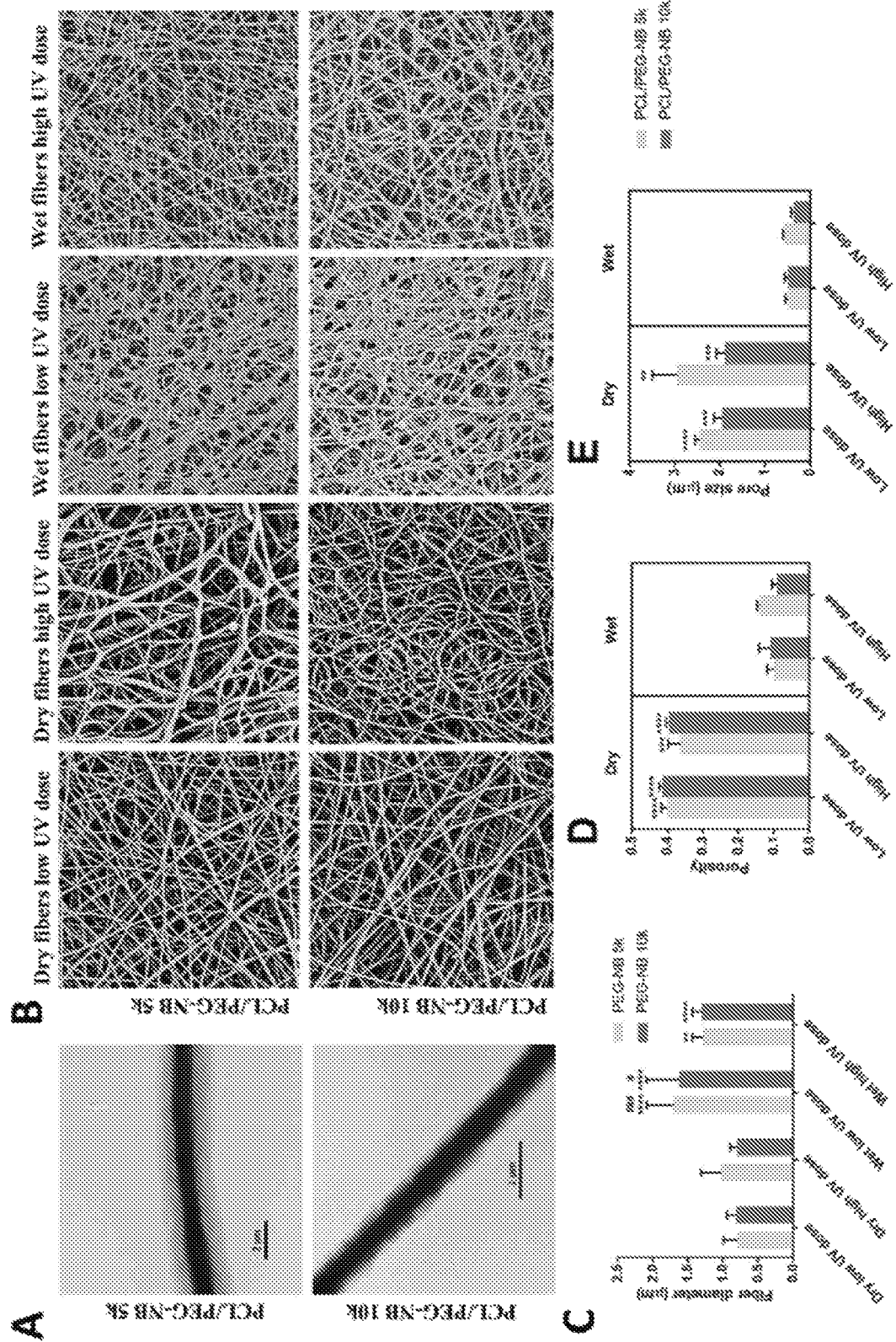
FIG. 3 B shows SEM images of coaxial fiber scaffolds, which were polymerized at different UV doses and stored in either dry or hydrated conditions.
Figure 4:
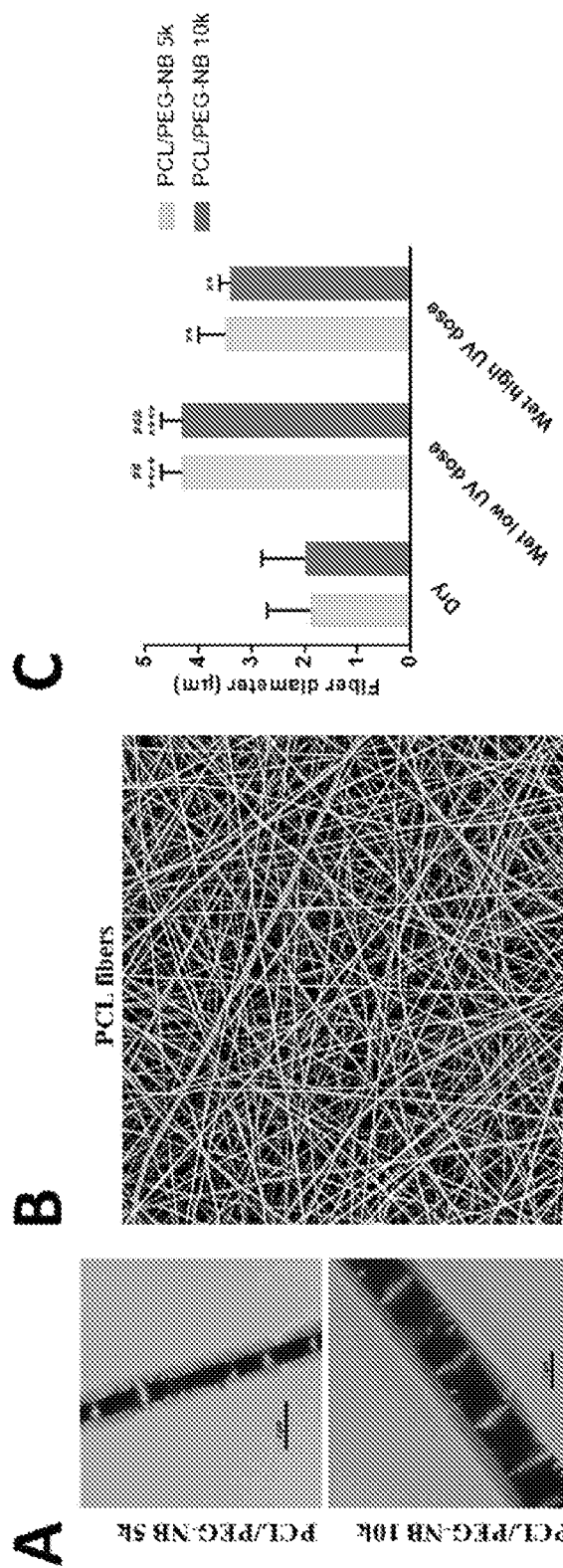
FIG. 4A-C shows electron microscopy images and quantitative analyses of coaxially-structured and PCL fibers.
Figure 5:
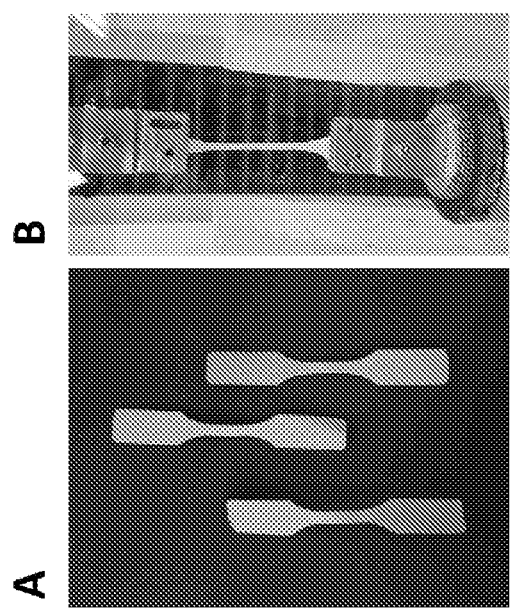
FIGS. 5A&B show dogbone-shaped fiber samples.
FIG. 5B shows wet samples during testing for their tensile strength.

The morphology of fabricated fiber scaffolds was characterized by electron microscopy (FIG. 3A-E). FIG. 3A shows the TEM images of the coaxial fibers with the core made of PCL and the sheath made from PEG-NB 5 k or PEG-NB 10 k. It demonstrates the successful formation of continuous coaxial PCL/PEG thiol-ene fibers. For both coaxial materials, we applied the flow rates of 0.8 mL h$^{-1}$ and 1 mL h$^{-1}$ for the core and sheath prepolymer fluids, respectively. The formation of continuous fibers was through our parametric studies of the coaxial electrospinning process. FIG. 4 illustrates another set of study, where the sheath fluid rate was increased to 1.3-1.4 mL h$^{-1}$, resulting in the discontinuity of the core fiber structure. This might be due to the high shear force produced by the more viscous sheath solution, longitudinally stretching the less viscous core solution and causing breakages in the core structure by rupturing the core material cohesion.

Table 3 shows the fiber diameter, core diameter, and sheath thickness measured from the TEM images, together with the sheath-to-fiber diameter ratios. To calculate the average sheath-to-fiber diameter ratio of fibers, the average sheath thickness was divided by the average fiber diameter. To obtain the standard deviation of this ratio, we reported the standard deviations for the sheath-to-fiber diameter ratios from individual fibers. Table 3 demonstrates that the sheath to-diameter ratio for PCL/PEG-NB 5 k is larger than PCL/PEG-NB 10 k, while their average fiber diameters are similar. The ratio difference is due to a thicker sheath and smaller sized core of PCL/PEG-NB 5 k, compared to PCL/PEG-NB 10 k. This might be related to the difference in the core-sheath interactions. The molecular interactions between core and sheath solutions may explain the finding about thicker sheath and higher sheath-to-diameter ratio in PCL/PEG-NB 5 k fibers compared to PCL/PEG-NB 10 k fibers. Compared to PCL/PEG-NB 10 k, the presence of a larger number of shorter chains in PEG-NB 5 k sheath could initiate a higher level of noncovalent bonding (stronger interaction between the core and the sheath solutions), leading to a thicker PEG-NB 5 k sheath in PCL/PEG-NB 5 k fibers. The polymer solution viscosity and solvent evaporation rate might play additional roles [32-34]. It is also found that the sheath thickness is not completely homogenous through coaxial fibers, which might be caused by varied surface energies between the core and sheath [35], affecting their adhesions.

TABLE 3

Sheath-to-fiber diameter ratio of coaxial fibers

| Scaffold material | Fiber diameter [μm] | Core diameter [μm] | Sheath thickness [μm] | Sheath-to-fiber diameter ratio |
|---|---|---|---|---|
| PCL/PEG-NB 5k | 2.5 ± 0.3 | 0.8 ± 0.1 | 1.8 ± 0.2 | 0.7 ± 0.1 |
| PCL/PEG-NB 10k | 2.5 ± 0.9 | 1.3 ± 0.5 | 1.4 ± 0.5 | 0.6 ± 0.3 |

FIG. 3B shows the SEM images of the coaxial fibers polymerized with varied UV dose in dry or wet states. Quantitative analysis results are shown in FIG. 3C-E. The coaxial fibers of PCL/PEG-NB 5 k and PCL/PEG-NB 10 k display similar diameters, porosity and pore size in dry or wet states. For both coaxial fibers, the diameters of wet fibers are significantly larger than dry fibers, due to water adsorption (FIG. 3C). Consequently, the swollen fiber scaffolds display decreased pore size and porosity, with respect to the dry scaffolds (FIG. 3D and FIG. 3E). Regarding the UV dose effect, results demonstrate that a lower UV dose (10 min of polymerization) leads to a larger fiber diameter and thus higher water retention in the coaxial fibers for PCL/PEG-NB 5 k and 10 k (FIG. 3C). This might be due to fewer interconnected PEG-NB molecules in less cross-linked fibers, which permit more water penetration and yield thicker fibers. Also, coaxial fiber swelling is only attributed to the hydrophilic sheath. Table 4 shows the sheath increase after hydration, confirming the polymerization effect on fiber swelling. The SEM image of PCL fibers is shown in FIG. 3B. Interestingly, the fiber diameter, pore size and porosity of PCL only fibers are much smaller than those of dry coaxial fibers. Fiber diameter results from optical images agree with those obtained from SEM images, and they are shown in FIG. 3C.

TABLE 4

Sheath increase after hydration of coaxial fibers

| UV dose | PCL/PEG-NB 5k sheath increase [%] | PCL/PEG-NB 10k sheath increase [%] |
|---|---|---|
| Wet low UV dose | 167 ± 38% | 193 ± 31% |
| Wet high UV dose | 111 ± 66% | 114 ± 142% |

Figure 7:
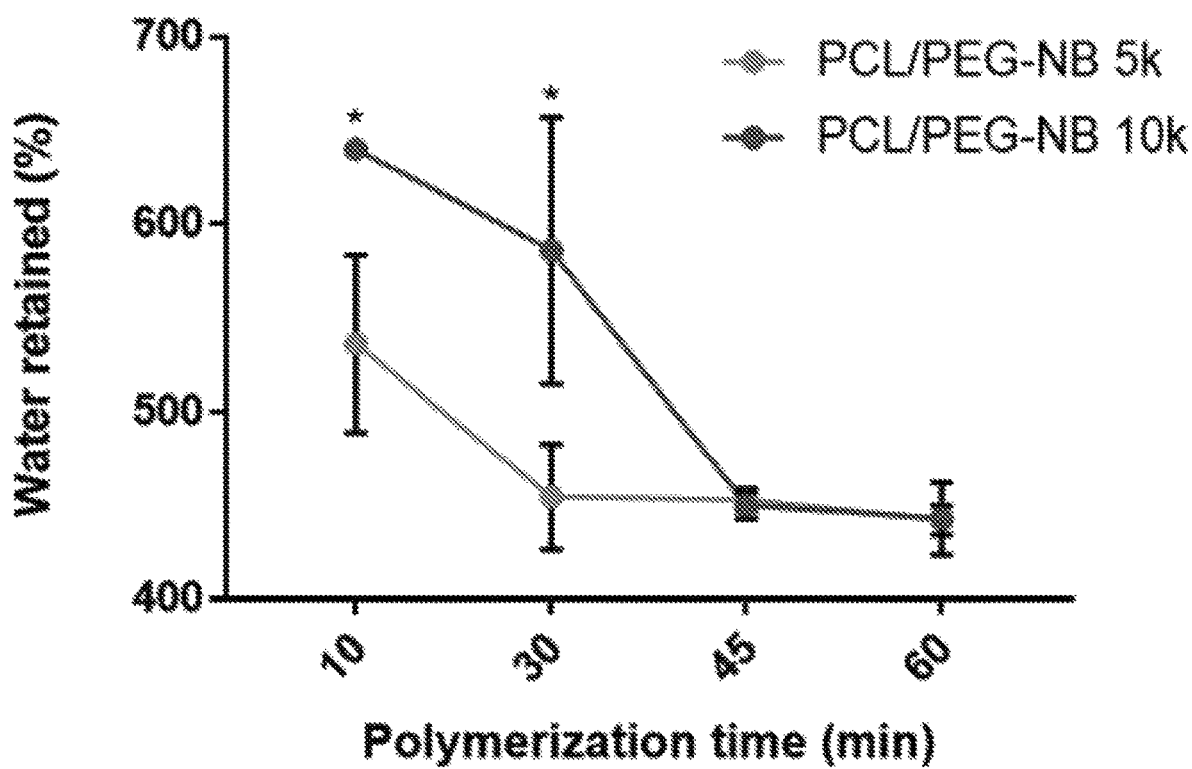
FIG. 7 shows the percentage of water retained after 10, 30, 45, and 60 min of cross-linking of the coaxial fibers. '*': comparing vs. the PCL/PEG-NB 5 k.

The coaxial fiber scaffolds display hydrogel-like swelling behaviors, varying with polymerization To characterize the swelling behaviors of coaxial fiber scaffolds, the water retention of scaffolds polymerized by varied UV doses (10, 30, 45 and 60 min of polymerization) was measured. Results regarding the UV dose effect on scaffold swelling (FIG. 7) are consistent with those from individual fiber swelling (FIG. 3C). Increased UV dose decreases the water retention of scaffolds, with the lowest dose yielding highest water retention. Both fiber swelling and increased water retained in the interfibrillar space could account for this water retention. However, water retained in the interfibrillar space might be quite limited, because FIG. 3D and FIG. 3E shows that both PCL/PEG-NB 5 k and 10 k scaffolds display lower pore size and porosity after hydration, resulting in denser fiber nets. Interestingly, the water retention of PCL/PEG-NB 10 k is higher than PCL/PEG-NB 5 k at the UV doses of 10 min and 30 min. This may be related to the longer reactive arms of the higher molecular weight PEG-NB 10 k, which make polymer chains more spatially separated, creating more spaces for water retention.

Another possible explanation is that PEG-NB 5 k presents twice as many reactive norbornene groups as PEG-NB 10 k, resulting in higher crosslink density. After 45 min, the polymerization in both scaffolds was complete, as their water retentions kept constant at similar values, which further validated the relationship between crosslinking and swelling.

The scaffolds are mechanically strong and viscoelastic materials

Figure 6:
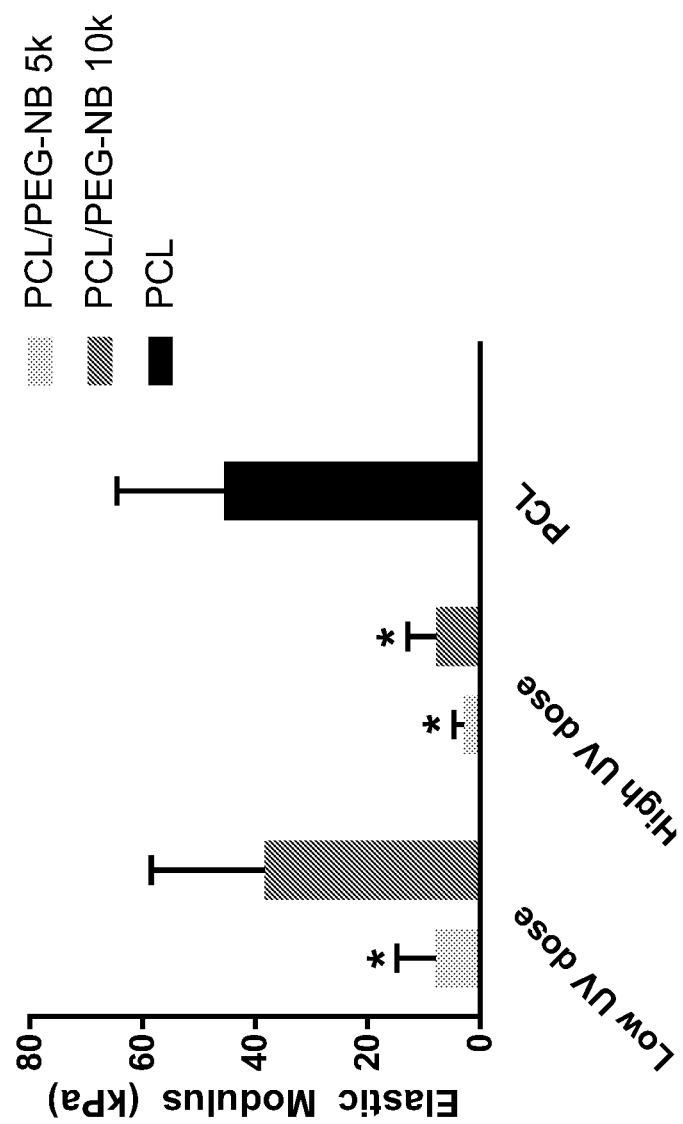
FIG. 6 shows the mlastic modulus of coaxial fibrous scaffolds composed of PCL/PEG-NB 5 k, PCL/PEG-NB 10 k, and PCL. '*' comparing vs. PCL control.
Figure 8:
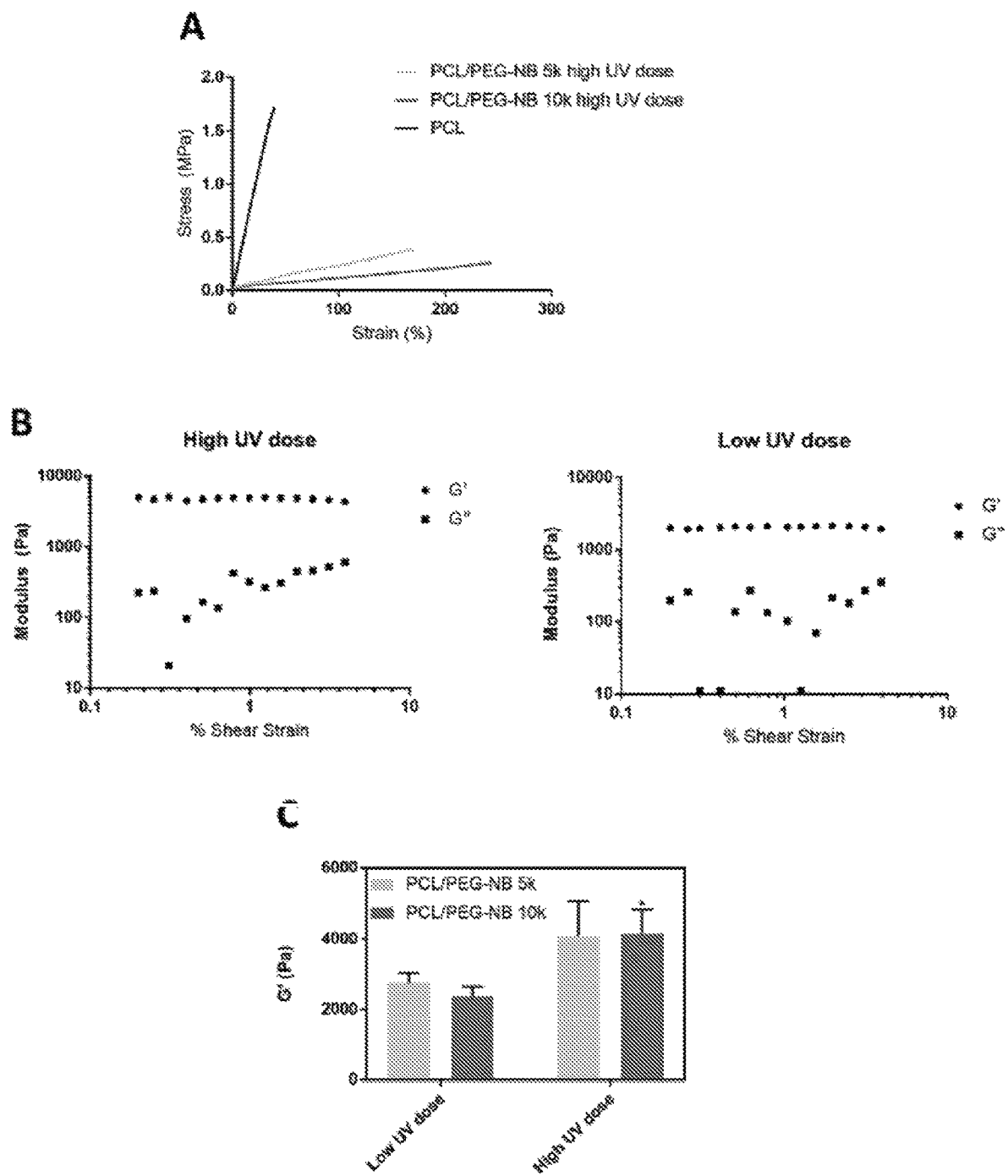
FIG. 8A-C shows Tensile and viscoelastic properties of PCL/PEG-NB coaxially-structured fibrous scaffolds polymerized with different UV doses.

Results from tensile tests performed in the hydrated condition on coaxial fiber scaffolds polymerized with a high UV dose are shown in Table 5 and FIG. 6 with representative stress-strain curves in FIG. 8A. The hydrated scaffolds polymerized with a low UV dose were weaker and easily slipping off the clips due to extremely high water contents, resulting in highly variable results (not shown here). The curve for PCL fiber scaffold is also shown for comparison. Tensile test results demonstrate that the coaxial fiber scaffolds are highly elastic and tough. When compared to PCL/PEG-NB 10 k scaffolds, PCL/PEG-NB 5 k scaffolds exhibit higher Young's modulus and fracture strength as well as lower strain at fracture. This can be attributed to the difference in the molecular size and bond formation. As PEG-NB 5 k solution contains up to twice as many reactive norbornene arms as PEG-NB 10 k, PEG-NB 5 k can be more reactive than PEG-NB 10 k, resulting in a more crosslinked structure with higher stiffness and strength. Also, PEG-NB 10 k molecules are longer than PEG-NB 5 k, likely creating more spaces in the hydrogel network for water softening. Therefore, the mechanical behaviors of PCL/PEG-NB 5 k vs. 10 k scaffolds in the wet condition agree with the water retention results. Additionally, the stiffness of PCL fibers is ~8-11 times higher, while the strain at fracture is ~4-6 times lower. The absence of thiol-ene hydrogel sheath leads to stiff, brittle behaviors of PCL fibers.

| Tensile properties | PCL | PCL/PEG-NB 5k | PCL/PEG-NB 10k |
|---|---|---|---|
| Maximum stress [kPa] | 1466.3 ± 230.5 | 419.6 ± 63.9 (*) | 265.6 ± 41.5 (*, #) |
| Maximum strain [%] | 44.7 ± 8.3 | 176.5 ± 7.6 (*) | 255.6 ± 34 (*, #) |
| Young's modulus [kPa] | 3529.5 ± 69.1 | 428.1 ± 86.2 (*) | 310.1 ± 30.2 (*) |

Figure 9:
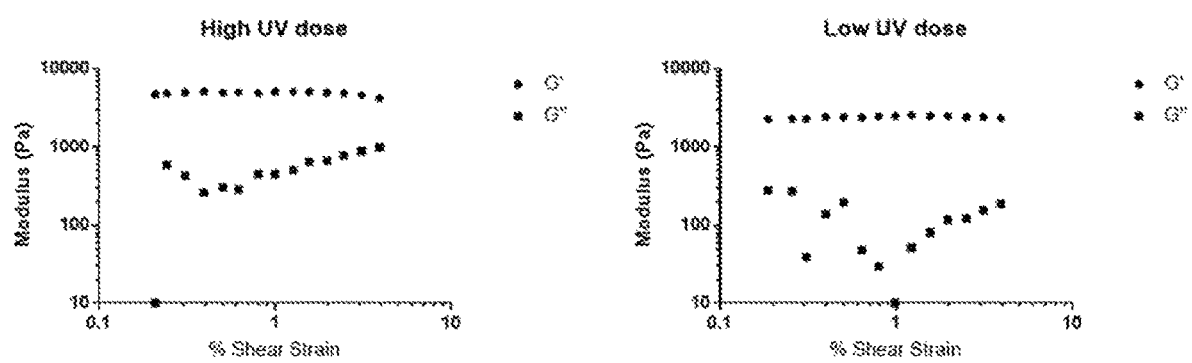
FIG. 9 shows viscoelastic property measurements of PCL/PEG-NB 5 k scaffold polymerized with high and low UV dose. Representative strain sweep results of G' and G", from the rheometer measurements.

Because of the hydrogel nature of coaxial fiber scaffolds, their viscoelastic behaviors were examined with rheometry using strain sweep (FIG. 8B and FIG. 9). The elastic behaviors were dominant in all cross-linked scaffolds, with the storage modulus (G') greater than the loss modulus (G"). The effects of UV dose and molecular weight of PEG-NB sheath were respectively studied (FIG. 8C), using the G' values in the linear region (shear strain=1%) for comparisons. For both PCL/PEG-NB 5 k and 10 k, a low UV dose resulted in a lower G', about half of high UV dose scaffolds. Higher dose yielded increased crosslinking among coaxial fibers and reduced water retention in the scaffolds, thus leading to stronger materials. Consistent with fiber and scaffold swelling behaviors, the difference in the storage modulus between PCL/PEG-NB 5 k and 10 k was not significant. However, limitations in this elasticity measurement must be acknowledged. Herein, coaxial fibers form a discontinuous hydrogel-like network, instead of a continuous material (i.e. composite) that can be properly evaluated using rheometry. This may explain some discrepancies between tensile modulus and storage modulus. Also, when G', which shows the in-phase response of a material to the applied strain, is highly relative to G" illustrating the out-of-phase response, G" is difficult to detect. This is especially true when the strain is relatively low, as done here. The noisy signals in the G" values illustrate such difficulty with G" detection approaching the transducer limit of the instrument.

Overall, the coaxial fiber scaffolds are mechanically strong and viscoelastic, comparable to soft tissues such as arteries. The tensile properties of PCL/PEG-NB scaffolds match well with those of natural arteries reported in the literature, including arteries' modulus (~200-400 kPa), strength (~150-1400 kPa), and maximum elongation (~45%-175%) [36-38]. Also, the stress-strain curves of coaxial fibers present a more linear behavior as opposed to hyper-elastic materials, probably due to the interfibrous crosslinks formed during polymerization, which effectively hinder a widespread alignment of the fibers before fracture occurs. The PCL core plays an essential role in stabilizing and strengthening these hydrogel scaffolds, which otherwise would collapse with extremely low modulus under wet conditions. The polymerization process makes scaffolds mechanically stronger due to not only interfibrillar cross-links, but also the intrafibrillar interactions mostly in the sheath. PCL/PEG-NB 5 k fibers likely present tighter and higher number of intra- and inter-fibrillar crosslinks than PCL/PEG-NB 10 k.

Thermal analysis of the coaxial fibers, showing coresheath interaction

Figure 10:
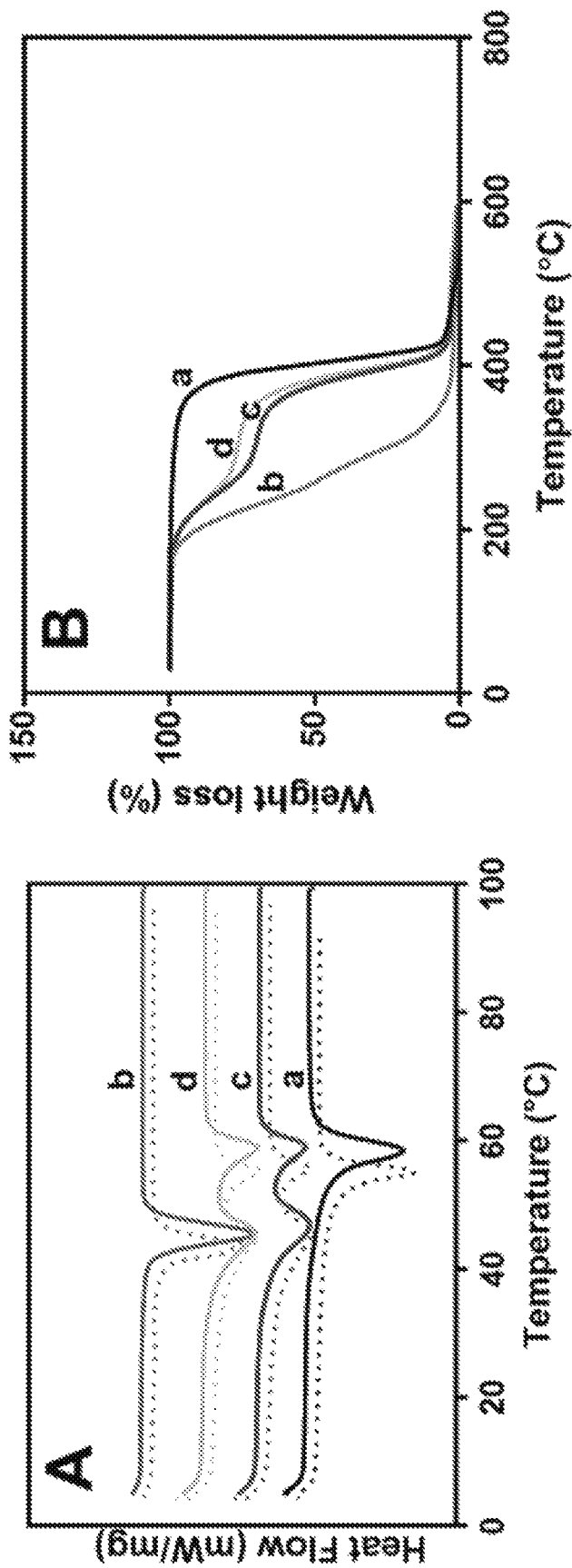
FIGS. 10A&B shows thermogravimetric analysis results. DSC (FIG. 10A), and TGA (FIG. 10B) measurements of individual polymer fibers and their coaxially spun fibers: (a) PCL, (b) PEG-NB 10 k, and (c-d) coaxial fibers of PCL/PEG-NB 10 k, polymerized with high (c) or low (d) UV dose.
Figure 11:
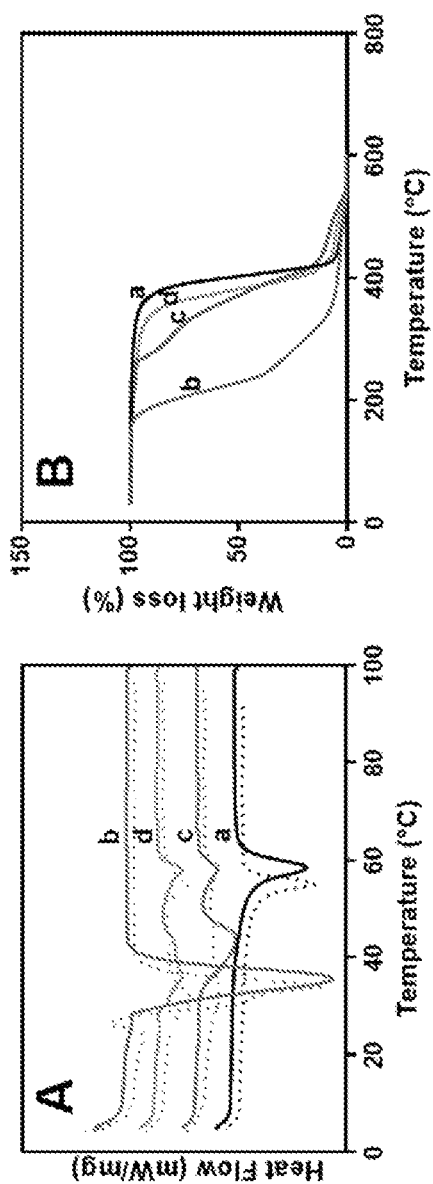
FIGS. 11A&B shows results from DSC (FIG. 11A) and TGA (FIG. 11B) measurements of individual polymers and their coaxial fibers. (a) PCL, (b) PEG-NB 5 k, (c-d) PCL/PEG-NB 5 k coaxial fibers polymerized at high (c) or low (d) UV dose.

FIG. 10A shows DSC measurements of individual polymers and their coaxial PCL/PEG-NB fibers. First (solid lines) and second (dashed lines) heating curves are both presented. Melting of PCL and PEG-NB 10 k occurs at around 60° C. and 45° C., respectively, during the endothermic processes in both heating curves [39]. The second peak, shifting to lower temperatures with respect to the first, is more reliable as it allows the evaluation of the inherent material properties [40]. The first peak can be influenced by the thermal history, production, impurities and crystallinity of polymer. The DSC curves of the coaxial fibers show two clear peaks, which correspond to the individual polymers but appear to be smaller than those counterparts, due to their lower weight percent. Additionally, the endothermic peaks for PCL in the coaxial fibers are less intense in the more polymerized coaxial fibers (FIG. 10A and FIG. 11A). This may be because (a) more cross-linked sheath better retains the heat in the polymeric core leading to a faster PCL core degradation, and (b) UV exposure may influence PCL degradation [10]. Notably, the glass transition temperature of PCL is −60° C., below the minimum temperature covered by the cooling cycle range.

FIG. 10B shows TGA analyses of individual polymers and their coaxial PCL/PEG-NB fibers. It is found that both PCL and PEG-NB 10 k show only one weight-loss step, while the coaxial PCL/PEG-NB fibers polymerized with both UV doses show two well-defined steps. For individual polymers, PCL fibers start to degrade at ~350° C., showing an abrupt decrease in weight, while PEG-NB start to degrade at ~200° C. with a slower decrease in weight. The two-step, weight-loss TGA curves for the coaxial PCL/PEG-NB fibers correspond to those of PCL and PEG-NB, showing a similar pattern with a main difference in the second step related to PCL degradation. PCL degrades at a lower temperature in PCL/PEG-NB 10 k coaxial fibers, compared to that in PCL fibers. This could be due to mechanical pressure and heat transfer from the sheath (PEG-NB 10 k) to the core (PCL) leading to a faster core degradation. High surface-volume ratio of core and sheath further promotes the heat transfer

[10]. Additionally, the degradation of the PCL core occurs faster in the network that has been polymerized for longer time. This could be due to the higher degree of crosslinking which does not allow the energy or heat to dissipate as much, leading to a faster melting of the fiber's core [41]. Finally, the fact that the two steps that correspond to the blend's single components are not merged but very well-defined in the TGA spectra indicates that there is no chemical reaction between them [10]. As all peaks in the TGA and DSC data correspond well to the constituting components of the coaxial fibers, thermal analysis results suggest that the core-sheath interactions might be limited to probably mechanical interlocking and physical entanglement. FIG. 11A&B shows results from DSC (A) and TGA (B) measurements of PCL/PEG-NB 5 k, which follow similar trends.

In vivo evaluation showing unprecedented cell penetration and ECM formation in coaxial fiber scaffolds To evaluate cell-material interaction, soft tissue healing and regeneration in the developed coaxial scaffolds in vivo, the scaffolds were implanted subcutaneously into rats for one week and the explants were analyzed by H&E and Masson's trichrome assays. H&E staining results show that a larger number of cells penetrated deep into the coaxial scaffolds, while only a thin cell layer coated the PCL matrix within 7 days after implantation (FIG. 22A). Further, trichrome staining results show more collagen-rich fibrotic tissue (FIG. 22A) in the stiffer coaxial fiber scaffolds with respect to softer ones, which might be due to more cell penetration in stiffer scaffolds for ECM protein synthesis. To confirm this, DAPI staining was used to visualize cell nuclei (FIG. 22B). For PCL fiber scaffolds, only a monolayer of cells was found on either side of the scaffolds, while all coaxial fiber scaffolds permitted uniform, deep material penetration of cells, with stiffer scaffolds attracting more cells. This result agrees well with our in vitro cell study results.

To further assess the ECM production and determine the relationship between cell infiltration and ECM deposition, two-photon microscopy imaging was employed to visualize collagen and elastin content. Regarding the collagen production (FIG. 22B, using SHG mode), stiffer coaxial fiber scaffolds showed higher collagen content, which was consistent with trichrome staining results. Similar finding was shown in the elastin deposition (FIG. 22B, using TPEF mode). No or little depositions of collagen and elastin were found in PCL fiber scaffolds. To affirm the conclusion, the cell density and ECM production were quantitatively analyzed (FIG. 22C and FIG. 22D). The ECM productions were determined using the area percent of collagen and elastin in the tissue. The results demonstrate that higher ECM production in stiffer coaxial scaffolds was likely caused by more cell infiltration. The in vivo result agrees with our in vitro cell study results, except for a small discrepancy in the cell density. A possible mechanism underlying this might lie in the phenotypic difference in participating cells. Endothelial cells were used in vitro, while different types of cells, including endothelial cells, smooth muscle cells and fibroblasts, might be involved in tissue remodeling in vivo. Each cell type has its own preference to the matrix environment in terms of cell proliferation and matrix production, which might lead to slightly different outcomes in vivo. Nevertheless, the difference in the cell density and matrix production in vivo between PCL/PEG-NB 10 k and PCL/PEG-NB 5 k scaffolds at high UV dose is statistically insignificant. Our results thus suggest that the role of polymer molecular weight (5 k vs. 10 k) in the in vivo cell attachment was not as important as the UV dose. High matrix stiffness at high UV dose could be sufficient to promote extensive cell attachment in vivo, regardless of the polymer molecular weight.

Overall, PCL/PEG-NB coaxial fiber scaffolds show nice integration with surrounding tissues in vivo, presenting improved cell penetration, ECM production, tissue healing and regeneration with respect to PCL fiber scaffolds. In addition, more polymerized coaxial scaffolds show an even more pronounced increase in these reparative/regenerative characteristics. This could occur due to a more organized cytoskeleton, enhanced attachment and migration of ECM-producing cells such as myofibroblasts on relatively stiffer substrates compared to softer matrices [10, 42]. Herein, the properties of both PCL and PEG-NB are exploited to achieve excellent mechanical property and bioactivity.

To determine materials-induced inflammation, immunofluorescent staining with CD68 to detect the macrophage presence presence was used with DAPI counterstain (FIG. 23). Results show the absence of macrophages in the coaxial materials, while their presence is observed in the PCL fibers scaffold. The results suggest that PCL fiber material appear to be more reactive producing more inflammation than coaxial materials when implanted in the body. Cells infiltrated in the coaxial material are most likely ECM-producing cells based on the detection of fibrillar collagen and elastin in the materials. Though we stressed on the material stiffness on in vivo results, an alternative mechanism underlying cell-scaffold interactions in vivo may be related to the steric shielding effect of PEG. Less polymerized PEGNB-sheathed scaffolds retain more water, likely exhibiting elevated steric shielding. Thus, higher water retention in these scaffolds could prevent nonspecific absorption of ECM proteins, which potentially benefit vascular regeneration, by inhibiting platelet adhesion, thrombosis or protein-induced fibrosis. Therefore, future investigations should be performed to further assess the combined effects of steric shielding and matrix stiffness of PEGNB sheathed scaffolds on the vascular regeneration in vivo.

7 PCL/PEG-NB

In one embodiment, the invention contemplates a medical device, such as a stent, with a coating comprising a hydrophobic, degradable core with a coaxial sheath comprising PCL/PEG-NB.

TABLE 6

Sheath-to-fiber diameter ratio of coaxial fibers.

| | Fiber diameter (nm) | Core diameter (nm) | Sheath thickness (nm) | Sheath-to-fiber diameter ratio |
|---|---|---|---|---|
| 3% PCL/PEG-NB | 402 ± 109.8 | 222.8 ± 31.1 | 176 ± 99.8 | 0.41 ± 0.14 |
| 5% PCL/PEG-NB | 500.6 ± 77 | 261.7 ± 36.1 | 228.5 ± 73.1 | 0.45 ± 0.08 |

TABLE 7

Mechanical properties of cross-linked coaxial grafts measured with uniaxial tensile testing.

| | PCL | 3% PCL/PEG-NB | 5% PCL/PEG-NB |
|---|---|---|---|
| Maximum stress (kPa) | 10711.8 ± 2654.9 | 978.8 ± 415.5 (*) | 2102.8 ± 369.8 ( ###) |
| Maximum strain (%) | 74.3 ± 10.2 | 197.1 ± 17.2(*) | 304 ± 15.1 (* ###) |

TABLE 7-continued

Mechanical properties of cross-linked coaxial grafts measured with uniaxial tensile testing.

|  | PCL | 3% PCL/PEG-NB | 5% PCL/PEG-NB |
|---|---|---|---|
| Young's modulus (kPa) | 15859.9 ± 3543.8 | 1081.8 ± 460.6() | 2310.8 ± 284.3 ( ##) |

'*' comparing vs. PCL fibers,
'#' comparing vs. 3% PCUPEG-NB.
The statistical significance levels were set at p < 0.05 (*or #).

TABLE 8

Suture strength (maximum stress) of the cross-linked coaxial grafts measured with uniaxial tensile testing.

|  | PCL | 3% PCL/PEG-NB | 5% PCL/PEG-NB |
|---|---|---|---|
| Maximum stress (kPa) | 1308 ± 87 | 249 ± 41 (*) | 306.3 ± 35 (*) |
| Average suture strength (N) | 3.4 | 0.7 | 0.9 |

'*' comparing vs.PCL fibers.
The statistical significance levelswere set at p < 0.05 (*).

8 Other Applications, Uses and Advantages

In one embodiment, the invention contemplates a medical device, such as a stent, with a coating comprising a hydrophobic, degradable core with a coaxial sheath comprising polyethylene-glycol dimethacrylate. This nanostructured coating overcomes complexity of interfacial phenomena as implanted biomaterials and coating over implants when such medical devices are used. Such interfacial phenomena encounter in medical device use includes blood clotting, biocompatibility, cell-material interaction, chemical inertness, decomposition of biomaterial, and evidence of inflammatory cytokines upon implantation. Medical devices, such as stents, with this coating allows control over individual components at sub-millimeter scale (such as nanoscale) during fabrication. This coating has potential to be used as implant coatings by tuning production criteria based on required material or mechanical properties in the body. Other applications for the fabricated material include, but are not limited to use in biosensors, orthopedic joint and ligaments coatings, vascular grafts, and catheter coatings. In one embodiment, said hydrophobic, degradable core comprises a poly L-lactide acid core. The core can comprise other hydrophobic polymers such as polycaprolactone, polyurethane, or combination of hydrophobic polymers based on the desired design. In one embodiment, said coating further comprises a controlled release agent. In one embodiment, said coating further comprises a therapeutic agent such as heparin. In one embodiment, said therapeutic agent comprises an anti-proliferation agent. In one embodiment, said hydrophobic, degradable core provided controlled drug release. In one embodiment, said sheath integrates a surface signaling mechanism. The surface of composite nanofibrous coating has the capability of regulating the cellular activities, based on the design goal (here is inhibiting proliferation and attachment of targeted cells). In one embodiment, said surface signaling mechanism that simultaneously aids in regeneration. In one embodiment, said coating further comprises an interactive surface. Such an interactive surface provided by this coating means that the coating design may makes it possible to have cell-material interaction surface which can be tuned for specific targets and cell interactions. In one embodiment, said coating further comprises sub-millimeter scale (such as nanoscale) fibers. In one embodiment, said sub-millimeter scale (such as nanoscale) fibers provide a uniform surface. In one embodiment, said sub-millimeter scale (such as nanoscale) fibers comprise a cell recognition platform. In one embodiment, said coating has no delaminiation. Delamination can be a significant problem in coatings. In contrast, the nanofibrous structure of coating of the present invention has shown perfect integrity as oppose to delamination potential of other nanocomposite structures. At sub-millimeter scale (such as nanoscale), due to the specific design and production methodology, each individual nanofiber has kept its structure integrity where there is no separation occurring between components, particularly at hydrated condition. Such a design helps to produce nanofibers with confident of not losing material and mechanical properties. In addition, each nanofiber individual is a representative of bulk and not a random accumulated of produced fibers. In one embodiment, said coating has an elastic modulus ranging from 172 to 729 kPa. In one embodiment, said the elasticity of said polyethylene-glycol dimethacrylate sheath is tunable by varying the photopolymerization time.

Thus, specific compositions and methods of pro-healing, pro-regenerative nanofibrous coating for have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Stefanini, G. G. and Holmes, D. R. (2013) "Drug-Eluting Coronary-Artery Stents," *N. Engl. I Med.* 368(3), 254-265.
2. Garg, S. et al. (2010) "Endothelial Progenitor Cell Capture Stents: Will This Technology Find Its Niche in Contemporary Practice?," *Eur. Heart J.* 31(9), 1032-1035.
3. Wilson, W. M. and Cruden, L. M. (2013) "Advances in Coronary Stent Technology: Current Expectations and New Developments," *DovePress* 4, 85-96.
4. Curcio, A. et al. (2011) "Mechanisms of Smooth Muscle Cell Proliferation and Endothelial Regeneration after Vascular Injury and Stenting and Approach to Therapy," *Circ. J.* 75(6), 1287-1296.
5. Uchida, Y. et al. (2010) "Formation of Web- and Membrane-Like Structures on the Edges of Bare-Metal Coronary Stents," *Circ. J.* 74(9), 1830-1836.

6. Park, J. S. et al. (2007) "Mechanobiology of Mesenchymal Stem Cells and Their Use in Cardiovascular Repair," *Front. Biosci* 12, 5098-5116.
7. Dahan, N. et al. (2012) "Porcine Small Diameter Arterial Extracellular Matrix Supports Endothelium Formation and Media Remodeling Forming a Promising Vascular Engineered Biograft," *Tissue Eng. Part A* 18(3-4), 411-422.
8. Brown, B. N. et al. (2010) "Surface Characterization of Extracellular Matrix Scaffolds," *Biomaterials* 31(3), 428-437.
9. Duncombe, T. A. et al. (2016) "Hydrogel Pore-Size Modulation for Enhanced Single-Cell Western Blotting," *Adv. Mater.* 28(2), 327-334.
10. Boodagh, P. et al. (2016) "Evaluation of Electrospun PLLA/PEGDMA Polymer Coatings for Vascular Stent Material," *J. Biomater. Sci., Polym. Ed.* 27(11), 1086-1099.
11. Peloquin, J. et al. (2011) "Indentation Measurements of the Subendothelial Matrix in Bovine Carotid Arteries," *J. Biomech.* 44(5), 815-821.
12. Wen, J. H. et al. (2014) "Interplay of Matrix Stiffness and Protein Tethering in Stem Cell Differentiation," *Nat. Mater.* 13, 979.
13. Wingate, K. et al. (2012) "Compressive Elasticity of Three-Dimensional Nanofiber Matrix Directs Mesenchymal Stem Cell Differentiation to Vascular Cells with Endothelial or Smooth Muscle Cell Markers," *Acta Biomater.* 8(4), 1440-1449.
14. Byfield, F. J. et al. (2009) "Endothelial Actin and Cell Stiffness Is Modulated by Substrate Stiffness in 2D and 3D," *J. Biomech.* 42(8), 1114-1119.
15. Fu, W. et al. (2014) "Electrospun Gelatin/Pcl and Collagen/Plcl Scaffolds for Vascular Tissue Engineering," *Int. J. Nanomedicine* 9, 2335-2344.
16. Zhu, C. et al. (2014) "Characterization of a Co-Electrospun Scaffold of Hlc/Cs/Pla for Vascular Tissue Engineering," *Bio-Med. Mater. Eng.* 24(6), 1999-2005.
17. Jia, L. et al. (2013) "Biocompatibility Evaluation of Protein-Incorporated Electrospun Polyurethane-Based Scaffolds with Smooth Muscle Cells for Vascular Tissue Engineering," *J. Mater. Sci.* 48, 5113.
18. Zilla, P. et al. (2007) "Prosthetic Vascular Grafts: Wrong Models, Wrong Questions and No Healing," *Biomaterials* 28(34), 5009-5027.
19. Nagiah, N. et al. (2015) "Highly Compliant Vascular Grafts with Gelatin-Sheathed Coaxially Structured Nanofibers," *Langmuir* 31(47), 12993-13002.
20. Bäckström, S. et al. (2012) "Tailoring Properties of Biocompatible PEG-Dma Hydrogels with Uv Light," *Material Science and Applications* 3(6), 425-431.
21. Wingate, K. et al. (2014) "Synergism of Matrix Stiffness and Vascular Endothelial Growth Factor on Mesenchymal Stem Cells for Vascular Endothelial Regeneration," *Tissue engineering. Part A* 20(17-18), 2503-2512.
22. Tze-Man, K. et al. (1993) "Surface Characterization and Platelet Adhesion Studies of Plasma-Sulphonated Polyethylene," *Biomaterials* 14(9), 657-664.
23. Farhatnia, Y. et al. (2013) "Evolution of Covered Stents in the Contemporary Era: Clinical Application, Materials and Manufacturing Strategies Using Nanotechnology," *Biotechnol. Adv.* 31(5), 524-542.
24. Vroman, I. and Tighzert, L. (2009) "Biodegradable Polymers," *Materials* 2(2), 307-344.
25. Dutov, P. et al. (2016) "Measurement of Elastic Modulus of Collagen Type I Single Fiber," *PLoS. ONE* 11(1), e0145711.
26. Chang, Z. et al. (2018) "Nanomechanics and Ultrastructure of the Internal Mammary Artery Adventitia in Patients with Low and High Pulse Wave Velocity," *Acta Biomater.* 73, 437-448.
27. Kohn, J. C. et al. (2016) "Mechanical Heterogeneities in the Subendothelial Matrix Develop with Age and Decrease with Exercise," *J. Biomech.* 49(9), 1447-1453.
28. Liu, F. et al. (2016) "Distal Vessel Stiffening Is an Early and Pivotal Mechanobiological Regulator of Vascular Remodeling and Pulmonary Hypertension," *JCI insight* 1(8), e86987.
29. Inoue, T. and Node, K. (2009) "Molecular Basis of Restenosis and Novel Issues of Drug-Eluting Stents," *Circ. J.* 73(4), 615-621.
30. Chen, S. et al. (2010) "Surface Hydration: Principles and Applications toward Low-Fouling/Nonfouling Biomaterials," *Polymer* 51(23), 5283-5293.
31. Zhao, W. et al. (2013) "Diaphragmatic Muscle Reconstruction with an Aligned Electrospun Poly(E-Caprolactone)/Collagen Hybrid Scaffold," *Biomaterials* 34(33), 8235-8240.
32. Golecki, H. M. et al. (2014) "Effect of Solvent Evaporation on Fiber Morphology in Rotary Jet Spinning," *Langmuir* 30(44), 13369-13374.
33. Hamrang, A. and Howell, B. A. (2014) *Foundations of High Performance Polymers: Properties, Performance and Applications*, Apple Academic Press, ON, Canada.
34. Liu, C. et al. (2015) "A Comparison of Centrifugally-Spun and Electrospun Regenerated Silk Fibroin Nanofiber Structures and Properties," *RSC Advances* 5(119), 98553-98558.
35. Li, Y. et al. (2014) "Nanofibers Support Oligodendrocyte Precursor Cell Growth and Function as a Neuron-Free Model for Myelination Study," *Biomacromolecules* 15(1), 319-326.
36. Khamdaeng, T. et al. (2012) "*Arterial Stiffness Identification of the Human Carotid* Artery Using the Stress-Strain Relationship in vivo," *Ultrasonics* 52(3), 402-411.
37. Sommer, G. et al. (2018) "Mechanical Response of Human Subclavian and Iliac Arteries to Extension, Inflation and Torsion," *Acta Biomater.* 75, 235-252.
38. Vatankhah, E. et al. (2014) "Electrospun Tecophilic/Gelatin Nanofibers with Potential for Small Diameter Blood Vessel Tissue Engineering," *Biopolymers* 101(12), 1165-1180.
39. Speranza, V. et al. (2014) "Characterization of the Polycaprolactone Melt Crystallization: Complementary Optical Microscopy, Dsc, and Afm Studies," *Scientific World Journal* 2014, 9.
40. Mohomed, K. and Bohnsack, D. A. (2013) "Differential Scanning calorimetry (Dsc) as an Analytical Tool in Plastics Failure Analysis," *American Laboratory* 45(3), 20-23.
41. Yeh, C.-C. et al. (2011) "The Effect of Polymer Molecular Weight and Uv Radiation on Physical Properties and Bioactivities of Pcl Films," *Cell. Polym.* 30(5), 261-276.
42. Ladoux, B. and Mege, R.-M. (2017) "Mechanobiology of Collective Cell Behaviours," *Nat. Rev. Mol. Cell Biol.* 18, 743.

We claim:
1. A medical implant with a coating comprising a hydrophobic, degradable core with a coaxial sheath comprising at least one polyethylene-glycol derivative,
wherein said hydrophobic, degradable core comprises a poly L-lactide acid (PLLA) core, wherein said at least one polyethylene-glycol derivative of said coaxial sheath comprises polyethylene-glycol dimethacrylate (PEGDMA), wherein said coating comprises a hybrid fiber coating, wherein said medical implant comprises a vascular stent.

2. The medical implant of claim 1, wherein said coating further comprises a controlled release agent.

3. The medical implant of claim 1, wherein said coating further comprises a therapeutic agent.

4. The medical implant of claim 3, wherein said therapeutic agent comprises an anti-proliferation agent.

5. The medical implant of claim 1, wherein said hydrophobic, degradable core provides controlled drug release.

6. The medical implant of claim 1, wherein said sheath integrates a surface signaling mechanism.

7. The medical implant of claim 6, wherein said surface signaling mechanism is configured to simultaneously aid in regeneration.

8. The medical implant of claim 1, wherein said coating further comprises sub-millimeter scale fibers.

9. The medical implant of claim 8, wherein said sub-millimeter scale fibers provide a uniform surface.

10. The medical implant of claim 1, wherein said coating has no delamination.

11. The medical implant of claim 1, wherein said coating has an elastic modulus ranging from 100 to 1000 kPa.

\* \* \* \* \*